US012715925B2

(12) United States Patent
Jain et al.

(10) Patent No.: US 12,715,925 B2
(45) Date of Patent: Aug. 25, 2026

(54) METHODS OF ADMINISTERING CHIMERIC ANTIGEN RECEPTOR IMMUNOTHERAPY

(71) Applicant: Kite Pharma, Inc., Santa Monica, CA (US)

(72) Inventors: Rajul Jain, Santa Monica, CA (US); Remus Vezan, Los Angeles, CA (US)

(73) Assignee: Kite Pharma, Inc., Santa Monica, CA (US)

( * ) Notice: Subject to any disclaimer, the term of this patent is extended or adjusted under 35 U.S.C. 154(b) by 771 days.

(21) Appl. No.: 18/167,725

(22) Filed: Feb. 10, 2023

(65) Prior Publication Data

US 2023/0270785 A1 Aug. 31, 2023

Related U.S. Application Data

(63) Continuation of application No. 16/865,369, filed on May 3, 2020, now abandoned.

(60) Provisional application No. 62/944,903, filed on Dec. 6, 2019, provisional application No. 62/931,669, filed on Nov. 6, 2019, provisional application No. 62/868,262, filed on Jun. 28, 2019, provisional application No. 62/855,828, filed on May 31, 2019, provisional application No. 62/843,190, filed on May 3, 2019.

(51) Int. Cl.

| | |
|---|---|
| ***A61P 35/00*** | (2006.01) |
| ***A61K 31/573*** | (2006.01) |
| ***A61K 39/395*** | (2006.01) |
| ***A61K 40/11*** | (2025.01) |
| ***A61K 40/31*** | (2025.01) |
| ***A61P 35/02*** | (2006.01) |
| ***A61P 37/06*** | (2006.01) |
| ***C07K 14/705*** | (2006.01) |
| ***C07K 16/28*** | (2006.01) |

(52) U.S. Cl.

CPC .......... *C07K 16/2866* (2013.01); *A61K 40/11* (2025.01); *A61K 40/31* (2025.01); *A61P 35/02* (2018.01); *C07K 14/70503* (2013.01); *A61K 2239/38* (2023.05); *A61K 2239/48* (2023.05)

(58) Field of Classification Search

None

See application file for complete search history.

(56) References Cited

U.S. PATENT DOCUMENTS

| | | | | |
|---|---|---|---|---|
| 5,591,827 | A | 1/1997 | Brakenhoff et al. | |
| 5,728,388 | A | 3/1998 | Terman | |
| 5,827,642 | A | 10/1998 | Riddell et al. | |
| 6,040,177 | A | 3/2000 | Riddell et al. | |
| 6,319,494 | B1 | 11/2001 | Capon et al. | |
| 6,797,514 | B2 | 9/2004 | Berenson et al. | |
| 6,867,041 | B2 | 3/2005 | Berenson et al. | |
| 6,905,874 | B2 | 6/2005 | Berenson et al. | |
| 7,741,465 | B1 | 6/2010 | Eshhar et al. | |
| 8,562,991 | B2 | 10/2013 | Igawa et al. | |
| 9,855,298 | B2 | 1/2018 | Bot et al. | |
| 12,357,646 | B2 * | 7/2025 | Garcia | A61K 31/675 |
| 2002/0006409 | A1 | 1/2002 | Wood | |
| 2013/0287748 | A1 | 10/2013 | June et al. | |
| 2014/0050708 | A1 | 2/2014 | Powell et al. | |
| 2014/0099309 | A1 | 4/2014 | Powell, Jr. et al. | |
| 2014/0154228 | A1 | 6/2014 | Volk et al. | |
| 2014/0227237 | A1 | 8/2014 | June et al. | |
| 2015/0202286 | A1 | 7/2015 | June et al. | |
| 2016/0208001 | A1 | 7/2016 | Zugmaier et al. | |
| 2018/0312588 | A1 | 11/2018 | Wiltzius et al. | |
| 2018/0371093 | A1 | 12/2018 | Bilic et al. | |
| 2019/0151361 | A1 | 5/2019 | Wiezorek | |
| 2019/0194343 | A1 | 6/2019 | Durrant et al. | |
| 2020/0384027 | A1 | 12/2020 | Jain et al. | |
| 2021/0161959 | A1 * | 6/2021 | Bot | A61K 31/675 |
| 2022/0387492 | A1 * | 12/2022 | Bot | A61K 31/675 |
| 2024/0058381 | A1 * | 2/2024 | Wiezorek | A61P 35/00 |

FOREIGN PATENT DOCUMENTS

| | | |
|---|---|---|
| WO | WO-2008081035 | 7/2008 |
| WO | WO-2012079000 | 8/2012 |
| WO | WO-2012129514 | 9/2012 |
| WO | WO-2015120096 | 11/2015 |
| WO | WO 2017165571 A1 | 9/2017 |
| WO | WO-2018013918 | 1/2018 |
| WO | WO-2017070395 | 5/2018 |
| WO | WO-2018223101 | 12/2018 |

(Continued)

OTHER PUBLICATIONS

Topp et al. (2019) Journal of Clinical Oncology, vol. 37, No. 15 Supplement, Abstract No. 7558.*
Locke et al. (2019) The Lancer Oncology 20:1, 31-42.*
Neelapu et al. (2018) Nature Reviews Clinical Oncology 15, 47-62.*
Hay K.A. (2018) British Journal of Haematology, 183, 364-374.*
Le et al. (2018) The Oncologist 23: 943-947.*
Liu et al. (2018) Journal of Hematology & Oncology 11:121, 1-7.*
Shimabukuro-Vornhagen et al. (2018) Journal for Immuno Therapy of Cancer 6:56, 1-14.*
Wang et al. (2018) Biomarker Research 6:4, 1-10.*
"ACTEMRA® (tocilizumab) injection, for intravenous or subcutaneous use", URL: https://www.gene.com/download/pdf/actemra_prescribing.pdf, 2010, 63 pages.

(Continued)

*Primary Examiner* — Ilia I Ouspenski

(74) *Attorney, Agent, or Firm* — Sheppard Mullin Richter & Hampton LLP

(57) ABSTRACT

The disclosure provides cells comprising CD19-directed chimeric antigen receptor (CAR) genetically modified autologous T cell immunotherapy for the treatment of, e.g., relapsed or refractory large B-cell lymphoma after two or more lines of systemic therapy, including diffuse large B-cell lymphoma (DLBCL) not otherwise specified, primary mediastinal large B-cell lymphoma, high grade B-cell lymphoma, and DLBCL arising from follicular lymphoma. Some aspects of the disclosure relate to methods of treatment and monitoring following infusion of T cell therapy provided herein.

10 Claims, No Drawings

(56) References Cited

FOREIGN PATENT DOCUMENTS

| WO | WO-2019070680 | 4/2019 |
|---|---|---|
| WO | WO-2019079564 | 4/2019 |

OTHER PUBLICATIONS

Brudno et al., "Toxicities of chimeric antigen receptor T cells: recognition and management", Blood, 2016, vol. 127, No. 26, pp. 3321-3330.
Cammack et al., "The Oxford Dictionary of Biochemistry and Molecular Biology (Second Edition)", Biochemistry and Molecular Biology, 2007, vol. 35, No. 4, 1 page summary.
Casan et al., "Anti-CD20 monoclonal antibodies: reviewing a revolution", Human Vaccines & Immunotherapeutics, 2018, vol. 14, No. 12, pp. 2820-2841.
Chavez et al., "CAR T-cell therapy for B-cell lymphomas: clinical trial results of available products," Therapeutic Advances in Hematology 2019, vol. 10, pp. 1-20.
Cheson et al., "Recommendations for Initial Evaluation, Staging, and Response Assessment of Hodgkin and Non-Hodgkin Lymphoma: The Lugano Classification," Journal of Clinical Oncology 2014, vol. 32, No. 27, pp. 3059-3067.
Communication pursuant to Rules 70(2) and 70a(2) EPC for European Application No. 20801592.5 dated Jan. 11, 2023. 1 page.
Crump et al., "Outcomes in refractory diffuse large B-cell lymphoma: results from the international SCHOLAR-1 study", Blood, Oct. 19, 2017, vol. 130, No. 16, pp. 1800-1808.
Du et al., "Next-generation anti-CD20 monoclonal antibodies in autoimmune disease treatment", Autoimmunity Highlights, 2017, vol. 8, No. 12, pp. 1-12.
Examination Report for Gulf Co-Operation Council Patent Application No. 39675 dated Oct. 24, 2021. 4 pages.
Examiner's Requisition for Canadian Application No. 3,138,707 dated Dec. 6, 2022. 6 pages.
Extended European Search Report for European Application No. 20801592.5 dated Dec. 22, 2022. 10 pages.
Galon et al., J. Clin. Oncol. (May 2017) vol. 35, No. 15 suppl., Abstract 3025, ascopubs.org/doi/10.1200/JCO.2017.35.15_suppl.3025. 4 pages.
Gust et al. Endothelial Activation and Blood-Brain Barrier Disruption in Neurotoxicity after Adoptive Immunotherapy with CD19 CAR-T Cells. Published OnlineFirst Oct. 12, 2017; Cancer Discovery, 7(12): 1404-1419, DOI: 10.1158/2159-8290.CD-17-0698. (Year: 2017).
Hamilton, John A, "GM-CSF as a target in inflammatory/autoimmune disease: current evidence and future therapeutic potential", Expert Review of Clinical immunology, 2015, pp. 1-9.
Hartl et al., "Genetics: Principles and Analysis, Fourth Edition", Jones and Bartlett Publishers, 1998, 1367 pages.
Hunter et al., "CAR T-Cell Associated Neurotoxicity: Mechanisms, Clinicopathologic Correlates, and Future Directions", Journal of the National Cancer Institute, 2019, vol. 111, No. 7, pp. 646-654.
International Preliminary Report on Patentability for International Application No. PCT/US2018/056467 dated Apr. 21, 2020.
International Search Report and Written Opinion for International Application No. PCT/US2018/056467 dated Feb. 4, 2019.
International Search Report and Written Opinion for International Patent Application No. PCT/US2020/031231 mailed Aug. 11, 2020. 10 pages.
Juo, "Concise Dictionary of Biomedicine and Molecular Biology, 2nd edition", CRC press, 2002, 1 page summary.
Kochenderfer et al., Chemotherapy-Refractory Diffuse Large B-Cell Lymphoma and Indolent B-Cell Malignancies Can Be Effectively Treated With Autologous T Cells Expressing an Anti-CD19 Chimeric Antigen Receptor, J Clin Oncol, vol. 33, No. 6, pp. 540-549, published Aug. 25, 2014.
Kochenderfer et al., Construction and preclinical evaluation of an anti-CD19 chimeric antigen receptor, J Immunother 2009, 32(7):689-702.
Lackie, J.M., "The Dictionary of Cell & Molecular Biology, 5th Edition," Academic Press, May 2014, 2 page summary.
Lee et al., "Current concepts in the diagnosis and management of cytokine release syndrome", Blood, Jul. 10, 2014, vol. 124, No. 2, pp. 188-195.
Locke et al., "Long-term safety and activity of axicabtagene ciloleucel in refractory large B-cell lymphoma (ZUMA-1): a single-arm, multicentre, phase 1-2 trial", Lancet Oncol, 2018, pp. 1-12.
Locke et al., "Phase 1 Results of ZUMA-1: A Multicenter Study of KTE-C19 Anti-CD19 CAR T Cell Therapy in Refractory Aggressive Lymphoma", Molecular Therapy, Jan. 2017, vol. 25, No. 1, pp. 285-295.
Locke et al., Abstract CT019: Primary results from ZUMA-1: a pivotal trial of axicabtagene ciloleucel (axicel; KTE-C19) in patients with refractory aggressive non-Hodgkin lymphoma (NHL), Cancer Research (2017), vol. 77, Supplement 13:CT019. 4 pages.
Locke et al., Updated Phase 1 Results from ZUMA-1, Molecular Therapy vol. 24, Supplement 1, No. 745, May 2016 (Year: 2016).
Lu et al., A Rapid Cell Expansion Process for Production of Engineered Autologous CAR-T Cell Therapies. Human Gene Therapy Methods 2016, vol. 27, No. 6: pp. 209-218 (Year: 2016).
Morais et al. (1999) Brazilian Journal of Medical and Biological Research; 32: 1211-1215.
Nastoupil et al., "Axicabtagene ciloleucel (Axi-cel) CD19 chimeric antigen receptor (CAR) T-cell therapy for relapsed/refractory large B-cell lymphoma: real world experience," Blood (2018), 132 (Supplement 1): 91. 8 pages.
Neelapu et al. (2017) N Engl. J Med; 377: 2531-2544.
Neelapu et al., "Axicabtagene Ciloleucel CAR T-Cell Therapy in Refractory Large B-Cell Lymphoma", The New England Journal of Medicine, Dec. 28, 2017, vol. 377, No. 26, pp. 2531-2544.
Office Action for Israeli Application No. 287533 dated Jun. 2, 2022. 5 pages.
Park et al., Adoptive Transfer of Chimeric Antigen Receptor Redirected Cytolytic T Lymphocyte Clones in Patients with Neuroblastoma. Molecular Therapy 2007, vol. 15, No. 4, pp. 825-833 (Year: 2007).
Riegler et al., "Current approaches in the grading and management of cytokine release syndrome after chimeric antigen receptor T-cell therapy", Therapeutics and Clinical Risk Management, 2019, vol. 15, pp. 323-335.
Ruella et al., "Chimeric Antigen Receptor T cells for B Cell Neoplasms: Choose the Right CAR for You", Curr Hematol Malig Rep, Springler, 2016, 11:368-384, 17 pages.
Sadelain et al., "Targeting tumours with genetically enhanced T lymphocytes", Nature Reviews Cancer, Jan. 2003, vol. 3, pp. 35-45.
Sadelain et al., "The Basic Principles of Chimeric Antigen Receptor Design", Cancer Discovery, 2013, pp. 388-398.
Sano et al., "Safety and Efficacy of Axicabtagene Ciloleucel (Axi-Cel) in Older Patients: Results from the US Lymphoma Car-T Consortium", Hematological Oncology, 2019, vol. 37, No. S2, pp. 304-305.
Sharma et al., "A U.S. Food and Drug Administration Age Based Pooled Analysis of Cytokine Release Syndrome and Neurotoxicity in Subjects with Relapsed/Refractory Lymphoma Treated with Chimeric Antigen Receptor (CAR) T Cell Therapy," Blood 2018, 132 (Supplement 1): 4201. 7 pages.
Shipp et al., "A predictive model for aggressive non-Hodgkin's lymphoma", International Non-Hodgkin's Lymphoma Prognostic Factors Project, 1993, vol. 329, No. 14, pp. 987-994.
Wang et al. (2013) Leukemia; 27: 1902-1909.
Watkins et al., CD19-targeted immunotherapies for treatment of patients with non-Hodgkin B-cell lymphomas, Expert Opinion on Investigational Drugs 2018,vol. 27, No. 7, pp. 601-611.
Wicks et al., "Targeting GM-CSF in inflammatory diseases", Nature Reviews Rheumatology, Jan. 2016, vol. 12, pp. 37-48.
Levin A. et al. "Chimeric antigen receptor modified T cell therapy in B cell non-Hodgkin lymphomas", Am J Hematol., vol. 94, No. S1, pp. S18-S23.
Park J. H. et al. "CD19-targeted CAR T-cell therapeutics for hematologic malignancies: interpreting clinical outcomes to date", Blood, vol. 127, No. 26, pp. 3312-3320.
New Zealand Examination Report No. 1 dated Jul. 10, 2024, for New Zealand Application No. 781824, 6 pages.

(56) References Cited

OTHER PUBLICATIONS

New Zealand Examination Report No. 2 dated Jan. 16, 2025, for New Zealand Application No. 781824, 4 pages.

* cited by examiner

METHODS OF ADMINISTERING CHIMERIC ANTIGEN RECEPTOR IMMUNOTHERAPY

CROSS-REFERENCE TO RELATED APPLICATIONS

This application is a continuation of U.S. application Ser. No. 16/865,369, filed May 3, 2020, now abandoned, which claims benefit of priority to U.S. Provisional Application No. 62/944,903, filed on Dec. 6, 2019; U.S. Provisional Application No. 62/931,669, filed on Nov. 6, 2019; U.S. Provisional Application No. 62/868,262, filed on Jun. 28, 2019; U.S. Provisional Application No. 62/855,828, filed on May 31, 2019; and U.S. Provisional Application No. 62/843,190, filed on May 3, 2019, the content of all of which are incorporated into the instant disclosure by reference.

TECHNICAL FIELD

The present disclosure relates generally to T cell therapies and more specifically to CD19-directed genetically modified autologous T cell immunotherapies comprising chimeric antigen receptors (CARs).

BACKGROUND

Human cancers are by their nature comprised of normal cells that have undergone a genetic or epigenetic conversion to become abnormal cancer cells. In doing so, cancer cells begin to express proteins and other antigens that are distinct from those expressed by normal cells. These aberrant tumor antigens may be used by the body's innate immune system to specifically target and kill cancer cells. However, cancer cells employ various mechanisms to prevent immune cells, such as T and B lymphocytes, from successfully targeting cancer cells.

Chimeric antigen receptors (CARs), which comprise binding domains capable of interacting with a particular tumor antigen, allow T cells to target and kill cancer cells that express the particular tumor antigen.

SUMMARY

As described in detail below, the present disclosure is based, in part, on the surprising discovery that the administration methods disclosed herein identify and manage adverse side effects and safety of CAR T-cell immunotherapy. In addition, the present disclosure relates to immunotherapy or T cell therapy and methods of enhancing treatment outcome and/or response.

Any aspect or embodiment described herein may be combined with any other aspect or embodiment as disclosed herein. While the present disclosure has been described in conjunction with the detailed description thereof, the foregoing description is intended to illustrate and not limit the scope of the present disclosure, which is defined by the scope of the appended claims. Other aspects, advantages, and modifications are within the scope of the following embodiments/claims.

In one aspect, the disclosure provides a method of treating relapsed or refractory diffuse large B-cell lymphoma (DLBCL) not otherwise specified, primary mediastinal large B-cell lymphoma, high grade B-cell lymphoma, or DLBCL arising from follicular lymphoma after two or more lines of systemic therapy in a patient comprising: administering to the patient in need thereof axicabtagene ciloleucel suspension by intravenous infusion at a dose between about $1\times10^6$ and about $2\times10^6$ CAR-positive viable T cells per kg body weight up to a maximum dose of about $1\times10^8$ CAR-positive viable T cells, wherein axicabtagene ciloleucel is a CD19-directed genetically modified autologous T cell immunotherapy, comprising the patient's own T cells harvested and genetically modified ex vivo by retroviral transduction to express a chimeric antigen receptor (CAR) comprising an anti-CD19 single chain variable fragment (scFv) linked to CD28 and CD3-zeta co-stimulatory domains.

In another aspect, the disclosure provides a method of treating relapsed or refractory diffuse large B-cell lymphoma (DLBCL) and primary mediastinal large B-cell lymphoma (PMBCL), after two or more lines of systemic therapy in a patient comprising: administering to the patient in need thereof axicabtagene ciloleucel suspension by intravenous infusion at a dose between about $0.4\times10^8$ and about $2\times10^8$ CAR-positive viable T cells, wherein axicabtagene ciloleucel is a CD19-directed genetically modified autologous T cell immunotherapy, comprising the patient's own T cells harvested and genetically modified ex vivo by retroviral transduction to express a chimeric antigen receptor (CAR) comprising an anti-CD19 single chain variable fragment (scFv) linked to CD28 and CD3-zeta co-stimulatory domains.

In some embodiments, the intravenous infusion time is between 15 and 120 minutes. In some embodiments, the intravenous infusion time is up to 30 minutes. In some embodiments, the infusion volume is between 50 and 100 mL. In some embodiments, the infusion volume is about 68 mL. In some embodiments, the immunotherapy is infused from an infusion bag. In some embodiments, the infusion bag is agitated during the infusion. In some embodiments, the immunotherapy is administered within 3 hours after thawing.

In some embodiments, the suspension further comprises albumin. In some embodiments, albumin is present in an amount of about 2-3% (v/v). In some embodiments, albumin is present in an amount of about 2.5% (v/v). In some embodiments, albumin is human albumin. In some embodiments, the suspension further comprises DMSO. In some embodiments, DMSO is present in an amount of about 4-6% (v/v). In some embodiments, DMSO is present in an amount of about 5% (v/v).

In one aspect, the disclosure provides a method of treating relapsed or refractory large B-cell lymphoma after two or more lines of systemic therapy in a patient comprising: (a) administering to the patient in need thereof CD19-directed genetically modified autologous T cell immunotherapy; and (b) monitoring the patient following infusion for signs and symptoms of an adverse reaction. In some embodiments, the relapsed or refractory large B-cell lymphoma is diffuse large B-cell lymphoma (DLBCL) not otherwise specified, primary mediastinal large B-cell lymphoma, high grade B-cell lymphoma, or DLBCL arising from follicular lymphoma.

In some embodiments, the adverse reaction is selected from the group consisting of cytokine release syndrome (CRS), a neurologic toxicity, a hypersensitivity reaction, a serious infection, a cytopenia and hypogammaglobulinemia. In some embodiments, the signs and symptoms of adverse reactions are selected from the group consisting of fever, hypotension, tachycardia, hypoxia, and chills, include cardiac arrhythmias (including atrial fibrillation and ventricular tachycardia), cardiac arrest, cardiac failure, renal insufficiency, capillary leak syndrome, hypotension, hypoxia, organ toxicity, hemophagocytic lymphohistiocytosis/macrophage activation syndrome (HLH/MAS), seizure, encephalopathy, headache, tremor, dizziness, aphasia, delirium, insomnia anxiety, anaphylaxis, febrile neutropenia, thrombocytopenia, neutropenia, and anemia.

In some embodiments, the method further comprises administering an IL-6 receptor inhibitor. In some embodiments, the method further comprises administering an effective amount of tocilizumab to treat a symptom of an adverse reaction. In some embodiments, tocilizumab is administered at a dose of about 8 mg/kg intravenously. In some embodiments, tocilizumab is administered intravenously over about 1 hour. In some embodiments, tocilizumab is administered about every 8 hours. In some embodiments, tocilizumab is administered for no more than about 24 hours.

In some embodiments, the method further comprises administering a steroid (e.g. corticosteroid to treat a symptom of an adverse reaction) or improve safety. In some embodiments, the corticosteroid is at least one of methylprednisone or dexamethasone.

In some embodiments, methylprednisone is administered at a dose of about 1 mg/kg intravenously. In some embodiments, methylprednisone is administered twice daily. In some embodiments, methylprednisone is administered at a dose of about 1,000 mg per day intravenously. In some embodiments, methylprednisone is administered intravenously for about 3 days. In some embodiments, dexamethasone is administered at a dose of about 10 mg. In some embodiments, dexamethasone is administered intravenously about every 6 hours.

In some embodiments, the adverse reaction is cytokine release syndrome (CRS). In some embodiments, the monitoring for signs and symptoms of cytokine release syndrome (CRS) is at least daily for about 7 days following infusion. In some embodiments, the monitoring for signs and symptoms of cytokine release syndrome (CRS) is at least daily for about 8 days, about 9 days, or about 10 days following infusion. In some embodiments, the monitoring for signs and symptoms of cytokine release syndrome (CRS) is at least daily for about 10 days following infusion. In some embodiments, the monitoring for signs and symptoms of cytokine release syndrome (CRS) is for about 4 weeks following infusion.

In some embodiments, the adverse reaction is neurologic toxicity. In some embodiments, the monitoring for signs and symptoms of neurologic toxicity up to about 8 weeks following infusion.

In some embodiments, the method further comprises administering a non-sedating, anti-seizure medicine for seizure prophylaxis. In some embodiments, the non-sedating, anti-seizure medicine is levetiracetam.

In some embodiments, the adverse reaction is a cytopenia. In some embodiments, the cytopenia is thrombocytopenia, neutropenia, and/or anemia.

In some embodiments, the method further comprises administering at least one of erythropoietin, darbepoetin alfa, platelet transfusion, colony-stimulating factor (CSF), granulocyte colony-stimulating factor, filgrastim, pegfilgrastim, or granulocyte-macrophage colony-stimulating factor.

In some embodiments, the method further comprises measuring cytokine and chemokine levels. In some embodiments, the level of at least one of IL-6, IL-8, IL-10, IL-15, TNF-α, IFN-γ, and sIL2Rα is measured.

In one aspect, the disclosure provides a container comprising a suspension of CD19-directed genetically modified autologous T cells, about 5% dimethylsulfoxide (DMSO) and about 2.5% human albumin (v/v). In another aspect, the container comprises a suspension of between about $0.4\times10^8$-$2\times10^8$ CD19-directed genetically modified autologous T cells (CAR-positive viable T cells). In some embodiments, the container is a sterile infusion bag. In some embodiments, the infusion bag volume is about 100 mL, 250 mL, 500 mL, 750 mL, 1000 mL, 1500 mL, 2000 mL or 3000 mL.

In one aspect, the disclosure provides a method of treating relapsed or refractory large B-cell lymphoma after two or more lines of systemic therapy in a human comprising administering to the human in need thereof CD19-directed genetically modified autologous T cell immunotherapy comprising: (a) administering to the patient a composition comprising CD19-directed chimeric antigen receptor (CAR) positive viable T cells; (b) monitoring the patient following administration for signs and symptoms of an adverse reaction; and (c) if cytokine release syndrome (CRS) greater than Grade 2 is observed in (b), administering tocilizumab at a dose of about 8 mg/kg IV over 1 hour, repeating tocilizumab every 8 hours as needed if not responsive to IV fluids or increasing supplemental oxygen; (d) if CRS symptoms observed in (b) do not improve after 24 hours of (c), administering methylprednisolone about 1 mg/kg IV twice daily or administering equivalent dexamethasone dose and continuing corticosteroids use until the event is Grade 1 or less, then tapering over 3 days; (e) if CRS Grade 3 is observed in (b), administering tocilizumab at a dose of 8 mg/kg IV over 1 hour, repeating tocilizumab every 8 hours as needed if not responsive to IV fluids or increasing supplemental oxygen and administering methylprednisolone 1 mg/kg IV twice daily or administering equivalent dexamethasone dose and continuing corticosteroids use until the event is Grade 1 or less, then tapering over 3 days; and (f) if CRS Grade 4 is observed in (b), administering tocilizumab at a dose of about 8 mg/kg IV over 1 hour, repeating tocilizumab every 8 hours as needed if not responsive to IV fluids or increasing supplemental oxygen and administering about 1,000 mg IV methylprednisolone per day for 3 days.

In one aspect, the disclosure provide a method of treating relapsed or refractory large B-cell lymphoma after two or more lines of systemic therapy in a patient comprising administering to the patient in need thereof CD19-directed genetically modified autologous T cell immunotherapy comprising: (a) administering to the patient a composition comprising CD19-directed chimeric antigen receptor (CAR) positive viable T cells; (b) monitoring the patient following administration for signs and symptoms of an adverse reaction; and (c) if cytokine release syndrome (CRS) and/or neurologic toxicity is observed, managing cytokine release syndrome (CRS) and/or neurologic toxicity according to Table 1 and/or Table 2.

The disclosed methods are further illustrated by the following numbered non-limiting embodiments.

1. A method of treating relapsed or refractory diffuse large B-cell lymphoma (DLBCL) not otherwise specified, primary mediastinal large B-cell lymphoma, high grade B-cell lymphoma, or DLBCL arising from follicular lymphoma after two or more lines of systemic therapy in a patient comprising:

administering to the patient in need thereof axicabtagene ciloleucel suspension by intravenous infusion at a dose between about $1\times10^6$ and about $2\times10^6$ CAR-positive viable T cells per kg body weight up to a maximum dose of about $1\times10^8$ CAR-positive viable T cells, wherein axicabtagene ciloleucel is a CD19-directed genetically modified autologous T cell immunotherapy, comprising the patient's own T cells harvested and genetically modified ex vivo by retroviral transduction to express a chimeric antigen receptor (CAR) comprising an anti-CD19 single chain variable fragment (scFv) linked to CD28 and CD3-zeta co-stimulatory domains.

2. The method of embodiment 1, wherein:

the intravenous infusion time is between 15 and 120 minutes, or up to 30 minutes;

the infusion volume is between 50 and 100 mL, or about 68 mL; and/or the immunotherapy is infused from an infusion bag, optionally, wherein the infusion bag is agitated during the infusion; optionally, wherein the immunotherapy is administered within 3 hours after thawing.

3. The method of any one of embodiments 1-2, wherein the suspension:

further comprises albumin, optionally, wherein albumin is present in an amount of about 2-3% (v/v), or in an amount of about 2.5% (v/v); and optionally wherein albumin is human albumin; and/or further comprises DMSO.

4. A method of treating relapsed or refractory large B-cell lymphoma after two or more lines of systemic therapy in a patient comprising:

(a) administering to the patient in need thereof CD19-directed genetically modified autologous T cell immunotherapy, preferably, axicabtagene ciloleucel; and (b) monitoring the patient following infusion for signs and symptoms of an adverse reaction and/or safety.

5 The method of embodiment 4, wherein the relapsed or refractory large B-cell lymphoma is diffuse large B-cell lymphoma (DLBCL) not otherwise specified, primary mediastinal large B-cell lymphoma, high grade B-cell lymphoma, or DLBCL arising from follicular lymphoma.

6. The method of any one of embodiments 4-5, wherein the adverse reaction is selected from the group consisting of cytokine release syndrome (CRS), a neurologic toxicity, a hypersensitivity reaction, a serious infection, a cytopenia and hypogammaglobulinemia.

7. The method of embodiment 6, wherein the signs and symptoms of adverse reactions are selected from the group consisting of fever, hypotension, tachycardia, hypoxia, and chills, include cardiac arrhythmias (including atrial fibrillation and ventricular tachycardia), cardiac arrest, cardiac failure, renal insufficiency, capillary leak syndrome, hypotension, hypoxia, organ toxicity, hemophagocytic lymphohistiocytosis/macrophage activation syndrome (HLH/MAS), seizure, encephalopathy, headache, tremor, dizziness, aphasia, delirium, insomnia anxiety, anaphylaxis, febrile neutropenia, thrombocytopenia, neutropenia, and anemia.

8. The method of any one of embodiments 1-7, wherein the method further comprises administering an effective amount of an inhibitor, or combination of inhibitors, of GM-CSF, CSF1, GM-CSFR, or CSF1R to treat a symptom of an adverse reaction.

9. The method of embodiment 8, wherein:

(i) the GM-CSF inhibitor is selected from lenzilumab; namilumab (AMG203); GSK3196165/MOR103/otilimab (GSK/MorphoSys); KB002 and KB003 (KaloBios); MT203 (Micromet and Nycomed); MORAb-022/gimsilumab (Morphotek); or a biosimilar of any one of the same; E21R; and a small molecule;

(ii) the CSF1 inhibitor is selected from RG7155, PD-0360324, MCS110/lacnotuzumab), or a biosimilar version of any one of the same; and a small molecule; and/or (iii) the GM-CSFR inhibitor and the CSF1R inhibitor is/are selected from Mavrilimumab (formerly CAM-3001; MedImmune, Inc.); cabiralizumab (Five Prime Therapeutics); LY3022855 (IMC-CS4)(Eli Lilly), Emactuzumab, also known as RG7155 or R05509554; FPA008 (Five Prime/BMS); AMG820 (Amgen); ARRY-382 (Array Biopharma); MCS110 (Novartis); PLX3397 (Plexxikon); ELB041/AFS98/TG3003 (ElsaLys Bio, Transgene), SNDX-6352 (Syndax); a biosimilar version of any one of the same; and a small molecule.

10. The method of any one of embodiments 8-9, wherein the inhibitor, or combination of inhibitors, is selected from lenzilumab and mavrilimumab; optionally, wherein either lenzilumab or mavrilimumab are administered at 10 mg/kg (600 mg max), 20 mg/kg (1200 mg max), or 30 mg/kg (1800 mg max) via IP infusion; or 100 mg or 150 mg, subcutaneously, respectively.

11. The method of any one of embodiments 8-9, wherein at least one of the inhibitors, or combination of inhibitors of GM-CSF, CSF1, GM-CSFR, or CSF1R are administered on the same day as axicabtagene ciloleucel.

12. The method of any one of embodiments 8-11, wherein at least one of the inhibitors, or combination of inhibitors of GM-CSF, CSF1, GM-CSFR, or CSF1R is/are administered between 1 to 12 hours prior to the administration of axicabtagene ciloleucel, optionally, simultaneously.

13. The method of any one of embodiments 8-12, wherein at least one of the inhibitors, or combination of inhibitors of GM-CSF, CSF1, GM-CSFR, or CSF1R is/are administered more than once after the administration of axicabtagene ciloleucel.

14. The method of any one of embodiments 8-13, wherein axicabtagene ciloleucel is administered as a single IV infusion at a target dose of $2\times10^6$ CAR-positive viable T cells/kg (maximum permitted dose: $2\times10^8$ cells), and either lenzilumab or mavrilimumab are administered at 10 mg/kg (600 mg max), 20 mg/kg (1200 mg max), or 30 mg/kg (1800 mg max) via IP infusion; or 100 mg or 150 mg, subcutaneously, respectively.

15. The method of any one of embodiments 8-14, further comprising administering a steroid (e.g., a corticosteroid) to treat a symptom of an adverse reaction.

16. The method of any one of embodiments 4-15, wherein the adverse reaction is cytokine release syndrome (CRS).

17. The method of any one of embodiments 4-16, wherein the method comprises monitoring for signs and symptoms of cytokine release syndrome (CRS), optionally at least daily for about 7 days following infusion.

18. The method of embodiment any one of embodiments 4-17, wherein the adverse reaction is (1) neurologic toxicity, optionally, wherein the symptom of neurologic toxicity is encephalopathy, headache, tremor, dizziness, aphasia, delirium, insomnia, and/or anxiety, and/or (2) cytopenia.

19. The method of any one of embodiments 1-18, wherein the method further comprises administering a non-sedating, anti-seizure medicine for seizure prophylaxis; administering at least one of erythropoietin, darbepoetin alfa, platelet transfusion, filgrastim, or pegfilgrastim; and/or administering tocilizumab.

20. The method of any one of embodiments 1-19, further comprising measuring cytokine and chemokine levels before and/or after one or more of the administrations, optionally, wherein the level of at least one of IL-2, IL-6, IL-8, IL-10, IL-12p40/p70, IL-15, IL-17a, TNF-α, IFN-γ, GM-CSF, and sIL2Rα is measured.

21. The method of any one of embodiments 1-20, further comprising administering an effective amount of a corticosteroid and/or tocilizumab to treat a symptom of an adverse reaction.

22. The method of any one of embodiments 8-13, wherein axicabtagene ciloleucel is administered as a single IV infusion at a target dose of $2\times10^6$ CAR-positive viable T cells/kg (maximum permitted dose: $2\times10^8$ cells) on Day 0, and/or mavrilimumab is administered once at 3 mg/kg subcutaneously, OP/IP, or IV on Day 0.

23. The method of any one of embodiments 8-13, wherein axicabtagene ciloleucel is administered as a single IV infusion at a target dose of $2\times10^6$ CAR-positive viable T cells/kg (maximum permitted dose: $2\times10^8$ cells) on Day 0, and/or mavrilimumab is administered once at 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, or 30 mg/kg, subcutaneously, OP/IP, or IV on Day 0.

24. The method of embodiment 22 or 23, further comprising administering conditioning chemotherapy on Days −5 to −3, comprising fludarabine at 30 mg/m$^2$/day and cyclophosphamide at 500 mg/m$^2$/day.

25. A method of treating relapsed or refractory large B-cell lymphoma after two or more lines of systemic therapy in a human comprising administering to the human in need thereof CD19-directed genetically modified autologous T cell immunotherapy comprising:

(a) administering to the patient a composition comprising CD19-directed chimeric antigen receptor (CAR) positive viable T cells;

(b) monitoring the patient following administration for signs and symptoms of an adverse reaction; and (c) if cytokine release syndrome (CRS) greater than Grade 2 is observed in (b), administering tocilizumab at a dose of about 8 mg/kg IV over 1 hour, repeating tocilizumab every 8 hours as needed if not responsive to IV fluids or increasing supplemental oxygen;

(d) if CRS symptoms observed in (b) do not improve after 24 hours of (c), administering methylprednisolone about 1 mg/kg IV twice daily or administering equivalent dexamethasone dose and continuing corticosteroids use until the event is Grade 1 or less, then tapering over 3 days;

(e) if CRS Grade 3 is observed in (b), administering tocilizumab at a dose of 8 mg/kg IV over 1 hour, repeating tocilizumab every 8 hours as needed if not responsive to IV fluids or increasing supplemental oxygen and administering methylprednisolone 1 mg/kg IV twice daily or administering equivalent dexamethasone dose and continuing corticosteroids use until the event is Grade 1 or less, then tapering over 3 days; and (f) if CRS Grade 4 is observed in (b), administering tocilizumab at a dose of about 8 mg/kg IV over 1 hour, repeating tocilizumab every 8 hours as needed if not responsive to IV fluids or increasing supplemental oxygen and administering about 1,000 mg IV methylprednisolone per day for 3 days.

26. A method of treating relapsed or refractory large B-cell lymphoma after two or more lines of systemic therapy in a patient comprising administering to the patient in need thereof CD19-directed genetically modified autologous T cell immunotherapy comprising:

(a) administering to the patient a composition comprising CD19-directed chimeric antigen receptor (CAR) positive viable T cells;

(b) monitoring the patient following administration for signs and symptoms of an adverse reaction; and (c) if cytokine release syndrome (CRS) and/or neurologic toxicity is observed, managing cytokine release syndrome (CRS) and/or neurologic toxicity according to Table 1, Table 2, Example 2, and/or Example 3.

27. A method of treating relapsed or refractory large ALL in a patient comprising administering to the patient in need thereof CD19-directed genetically modified autologous T cell immunotherapy comprising:

(a) administering to the patient a composition comprising CD19-directed chimeric antigen receptor (CAR) positive viable T cells;

(b) monitoring the patient following administration for signs and symptoms of an adverse reaction; and (c) if cytokine release syndrome (CRS) and/or neurologic toxicity is observed, managing cytokine release syndrome (CRS) and/or neurologic toxicity according to Table 1, Table 2, Example 2, and/or Example 3.

28. A method of treating relapsed or refractory diffuse large B-cell lymphoma (DLBCL) not otherwise specified, primary mediastinal large B-cell lymphoma, high grade B-cell lymphoma, or DLBCL arising from follicular lymphoma in a patient in need thereof comprising:

administering to the patient in need thereof axicabtagene ciloleucel suspension by intravenous infusion at a dose between about $1\times10^6$ and about $2\times10^6$ CAR-positive viable T cells per kg body weight up to a maximum dose of about $1\times10^8$ CAR-positive viable T cells in combination with rituximab, wherein axicabtagene ciloleucel is a CD19-directed genetically modified autologous T cell immunotherapy, comprising the patient's own T cells harvested and genetically modified ex vivo by retroviral transduction to express a chimeric antigen receptor (CAR) comprising an anti-CD19 single chain variable fragment (scFv) linked to CD28 and CD3-zeta co-stimulatory domains.

29. The method of embodiment 28, wherein the patient receives rituximab 375 mg/m$^2$ on Day −5, and conditioning chemotherapy with fludarabine 30 mg/m$^2$ and cyclophosphamide 500 mg/m$^2$ on day −5, −4, and −3; followed by 2 days of rest on Day −2 and Day −1; followed by administration with axicabtagene ciloleucel, administered at a target dose of $2\times10^6$ anti-CD19 CAR T cells/kg on Day 0.

30. The method of embodiment 28, wherein the patient receives lenalidomide 10 mg daily starting 7 days after leukapheresis and continuing through Day 3 after axicabtagene ciloleucel infusion, followed by conditioning chemotherapy with fludarabine 30 mg/m$^2$ and cyclophosphamide 500 mg/m$^2$ on day −5, −4, and −3; followed by 2 days of rest on Day −2 and Day −1; followed by axicabtagene ciloleucel, administered at a target dose of $2\times10^6$ anti-CD19 CAR T cells/kg on Day 0.

31. The method of embodiment 28, wherein the patient is refractory to a first-line of therapy, refractory to second or greater lines of therapy, refractory after autologous stem cell transplant.

32. The method of any one of embodiments 28 through 31, wherein the patients have previously received Anti-CD20 mAb and an anthracycline-containing chemotherapy regimen.

33. The method any one of embodiments 28 through 32, wherein the patient further receives rituximab for 5 additional doses at 28-day intervals after axicabtagene ciloleucel infusion.

34. The method of anyone of embodiments 28 through 33, wherein the patient further receives lenalidomide 20 mg for 5 additional cycles at 28-day intervals (21 on treatment/28 days) after axicabtagene ciloleucel infusion.

35. The method of any one of embodiments 28 through 34, wherein the patient further receives mesna.

36. The method of any one of embodiments 8-13, wherein axicabtagene ciloleucel is administered as a single IV infusion at a target dose of $2\times10^6$ CAR-positive viable T cells/kg (maximum permitted dose: $2\times10^8$ cells) on Day 0, and mavrilimumab is administered once at 3 mg/kg of body weight subcutaneously, OP/IP, or IV on Day 0.

37. The method of any one of embodiments 8-13, wherein axicabtagene ciloleucel is administered as a single IV infusion at a target dose of $2\times10^6$ CAR-positive viable T cells/kg (maximum permitted dose: $2\times10^8$ cells) on Day 0, and/or mavrilimumab is administered once at 1 mg/kg of body weight, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, or 30 mg/kg, subcutaneously, OP/IP, or IV on Day 0.

38. The method of embodiment 36, further comprising administering conditioning chemotherapy on Days −5 to −3, comprising fludarabine at 30 mg/m$^2$/day and cyclophosphamide at 500 mg/m$^2$/day In one aspect, the disclosure is directed to a method of treating relapsed or refractory large B-cell lymphoma after two or more lines of systemic therapy in a human comprising administering to the human in need thereof CD19-directed genetically modified autologous T cell immunotherapy comprising: (a) administering to the patient a composition comprising CD19-directed chimeric antigen receptor (CAR) positive viable T cells; (b) monitoring the patient following administration for signs and symptoms of an adverse reaction; and (c) if cytokine release syndrome (CRS) greater than Grade 2 is observed in (b), administering tocilizumab at a dose of about 8 mg/kg IV over 1 hour, repeating tocilizumab every 8 hours as needed if not responsive to IV fluids or increasing supplemental oxygen; (d) if CRS symptoms observed in (b) do not improve after 24 hours of (c), administering methylprednisolone about 1 mg/kg IV twice daily or administering equivalent dexamethasone dose and continuing corticosteroids use until the event is Grade 1 or less, then tapering over 3 days; (e) if CRS Grade 3 is observed in (b), administering tocilizumab at a dose of 8 mg/kg IV over 1 hour, repeating tocilizumab every 8 hours as needed if not responsive to IV fluids or increasing supplemental oxygen and administering methylprednisolone 1 mg/kg IV twice daily or administering equivalent dexamethasone dose and continuing corticosteroids use until the event is Grade 1 or less, then tapering over 3 days; and (f) if CRS Grade 4 is observed in (b), administering tocilizumab at a dose of about 8 mg/kg IV over 1 hour, repeating tocilizumab every 8 hours as needed if not responsive to IV fluids or increasing supplemental oxygen and administering about 1,000 mg IV methylprednisolone per day for 3 days.

In one aspect, the disclosure is directed to a method of treating relapsed or refractory large B-cell lymphoma after two or more lines of systemic therapy in a patient comprising administering to the patient in need thereof CD19-directed genetically modified autologous T cell immunotherapy comprising: (a) administering to the patient a composition comprising CD19-directed chimeric antigen receptor (CAR) positive viable T cells; (b) monitoring the patient following administration for signs and symptoms of an adverse reaction; and (c) if cytokine release syndrome (CRS) and/or neurologic toxicity is observed, managing cytokine release syndrome (CRS) and/or neurologic toxicity according to Table 1, Table 2, Table 3, and/or Table 4.

In one aspect, the disclosure is directed to a method of treating relapsed or refractory large ALL in a patient comprising administering to the patient in need thereof CD19-directed genetically modified autologous T cell immunotherapy comprising: (a) administering to the patient a composition comprising CD19-directed chimeric antigen receptor (CAR) positive viable T cells; (b) monitoring the patient following administration for signs and symptoms of an adverse reaction; and (c) if cytokine release syndrome (CRS) and/or neurologic toxicity is observed, managing cytokine release syndrome (CRS) and/or neurologic toxicity according to Table 1, Table 2, Example 2, and/or Example 3.

Other features and advantages of the disclosure will be apparent from the following Detailed Description, including the Examples.

DETAILED DESCRIPTION

Definitions

In order for the present disclosure to be more readily understood, certain terms are first defined below. Additional definitions for the following terms and other terms are set forth throughout the Specification.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

The term "and/or" where used herein is to be taken as specific disclosure of each of the two specified features or components with or without the other. Thus, the term "and/or" as used in a phrase such as "A and/or B" herein is intended to include A and B; A or B; A (alone); and B (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The terms "e.g.," and "i.e." as used herein, are used merely by way of example, without limitation intended, and should not be construed as referring only those items explicitly enumerated in the specification.

The terms "or more", "at least", "more than", and the like, e.g., "at least one" are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides. Also included is any lesser number or fraction in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. It is understood that wherever aspects are described herein with the language "comprising," otherwise analogous aspects described in terms of "consisting of" and/or "consisting essentially of" are also provided.

Unless specifically stated or evident from context, as used herein, the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "approximately" may mean within one or more than one standard deviation per the practice in the art. "About" or "approximately" may mean a range of up to 10% (i.e., ±10%). Thus, "about" may be understood to be within 10%, 9%, 8%, 7%, 6%, 5%, 4%, 3%, 2%, 1%, 0.5%, 0.1%, 0.05%, 0.01%, or 0.001% greater or less than the stated value. For example, about 5 mg may include any amount between 4.5 mg and 5.5 mg. Furthermore, particularly with respect to biological systems or processes, the terms may mean up to an order of magnitude or up to 5-fold of a value. When particular values or compositions are provided in the instant disclosure, unless otherwise stated, the meaning of "about" or "approximately" should be assumed to be within an acceptable error range for that particular value or composition.

As described herein, any concentration range, percentage range, ratio range or integer range is to be understood to be inclusive of the value of any integer within the recited range and, when appropriate, fractions thereof (such as one-tenth and one-hundredth of an integer), unless otherwise indicated.

Units, prefixes, and symbols used herein are provided using their Système International de Unites (SI) accepted form. Numeric ranges are inclusive of the numbers defining the range.

Unless defined otherwise, all technical and scientific terms used herein have the same meaning as commonly understood by one of ordinary skill in the art to which this disclosure is related. For example, Juo, "The Concise Dictionary of Biomedicine and Molecular Biology", 2nd ed., (2001), CRC Press; "The Dictionary of Cell & Molecular Biology", 5th ed., (2013), Academic Press; and "The Oxford Dictionary Of Biochemistry And Molecular Biology", Cammack et al. eds., 2nd ed, (2006), Oxford University Press, provide those of skill in the art with a general dictionary for many of the terms used in this disclosure.

"Administering" refers to the physical introduction of an agent to a subject, using any of the various methods and delivery systems known to those skilled in the art. Exemplary routes of administration for the formulations disclosed herein include intravenous, intramuscular, subcutaneous (SQ), intraperitoneal, spinal or other parenteral routes of administration, for example by injection or infusion. The phrase "parenteral administration" as used herein means modes of administration other than enteral and topical administration, usually by injection, and includes, without limitation, intravenous (IV), intramuscular, intraarterial, intrathecal, intralymphatic, intralesional, intracapsular, intraorbital, intracardiac, intradermal, intraperitoneal (IP), transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering may also be performed, for example, once, a plurality of times, and/or over one or more extended periods. Where one or more therapeutic agents are administered, the administration can be done concomitantly or sequentially. Sequential administration comprises administration of one agent only after administration of the other agent or agents has been completed.

The term "antibody" (Ab) includes, without limitation, a glycoprotein immunoglobulin which binds specifically to an antigen. In general, an antibody may comprise at least two heavy (H) chains and two light (L) chains interconnected by disulfide bonds, or an antigen-binding molecule thereof. Each H chain comprises a heavy chain variable region (abbreviated herein as VH) and a heavy chain constant region. The heavy chain constant region comprises three constant domains, CH1, CH2 and CH3. Each light chain comprises a light chain variable region (abbreviated herein as VL) and a light chain constant region. The light chain constant region comprises one constant domain, CL. The VH and VL regions may be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component (C1q) of the classical complement system.

Antibodies may include, for example, monoclonal antibodies, recombinantly produced antibodies, monospecific antibodies, multispecific antibodies (including bispecific antibodies), human antibodies, engineered antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, antibody fusions (sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, F(ab')2 fragments, disulfide-linked Fvs (sdFv), dual $(ScFv)_2$-Fab, anti-idiotypic (anti-Id) antibodies (including, e.g., anti-anti-Id antibodies), minibodies, domain antibodies, synthetic antibodies (sometimes referred to herein as "antibody mimetics"), diabodies, IgG fusions (e.g., dual variable domain (DVD)-Ig), Fc fusions (e.g. ScFv/Fc fusions, immune mobilising mTCR, and antigen-binding fragments of any of the above. In some embodiments, antibodies described herein refer to polyclonal antibody populations.

An "antigen binding molecule," "antigen binding portion," or "antibody fragment" refers to any molecule that comprises the antigen binding parts (e.g., CDRs) of the antibody from which the molecule is derived. An antigen binding molecule may include the antigenic complementarity determining regions (CDRs). Examples of antibody fragments include, but are not limited to, Fab, Fab', F(ab')2, and Fv fragments, dAb, linear antibodies, scFv antibodies, and multispecific antibodies formed from antigen binding molecules. Peptibodies (i.e., Fc fusion molecules comprising peptide binding domains) are another example of suitable antigen binding molecules. In some embodiments, the antigen binding molecule binds to an antigen on a tumor cell. In some embodiments, the antigen binding molecule binds to an antigen on a cell involved in a hyperproliferative disease or to a viral or bacterial antigen. In some embodiments, the antigen binding molecule binds to CD19. In further embodiments, the antigen binding molecule is an antibody fragment that specifically binds to the antigen, including one or more of the complementarity determining regions (CDRs) thereof. In further embodiments, the antigen binding molecule is a single chain variable fragment (scFv). In some embodiments, the antigen binding molecule comprises or consists of avimers.

An "antigen" refers to any molecule that provokes an immune response or is capable of being bound by an antibody or an antigen binding molecule. The immune response may involve either antibody production, or the activation of specific immunologically-competent cells, or both. A person of skill in the art would readily understand that any macromolecule, including virtually all proteins or peptides, may serve as an antigen. An antigen may be endogenously expressed, i.e. expressed by genomic DNA, or may be recombinantly expressed. An antigen may be specific to a certain tissue, such as a cancer cell, or it may be broadly expressed. In addition, fragments of larger molecules may act as antigens. In some embodiments, antigens are tumor antigens.

"CD19-directed genetically modified autologous T cell immunotherapy" refers to a suspension of chimeric antigen receptor (CAR)-positive T cells. An example of such immunotherapy is axicabtagene ciloleucel (also known as Axi-cel™, YESCARTA®), developed by Kite Pharmaceuticals, Inc. Other non-limiting examples include JCAR017, JCAR015, JCAR014, Kymriah (tisagenlecleucel), Uppsala U. anti-CD19 CAR (NCT02132624), and UCART19 (Celectis).

The term "neutralizing" refers to an antigen binding molecule, scFv, antibody, or a fragment thereof, that binds to a ligand and prevents or reduces the biological effect of that ligand. In some embodiments, the antigen binding molecule, scFv, antibody, or a fragment thereof, directly blocking a binding site on the ligand or otherwise alters the ligand's ability to bind through indirect means (such as structural or energetic alterations in the ligand). In some embodiments, the antigen binding molecule, scFv, antibody, or a fragment thereof prevents the protein to which it is bound from performing a biological function.

The term "autologous" refers to any material derived from the same individual to which it is later to be re-introduced. For example, the engineered autologous cell therapy (eACT™) method described herein involves collection of lymphocytes from a patient, which are then engineered to express, e.g., a CAR construct, and then administered back to the same patient.

The term "allogeneic" refers to any material derived from one individual which is then introduced to another individual of the same species, e.g., allogeneic T cell transplantation.

The terms "transduction" and "transduced" refer to the process whereby foreign DNA is introduced into a cell via viral vector (see Jones et al., "Genetics: principles and analysis," Boston: Jones & Bartlett Publ. (1998)). In some embodiments, the vector is a retroviral vector, a DNA vector, a RNA vector, an adenoviral vector, a baculoviral vector, an Epstein Barr viral vector, a papovaviral vector, a vaccinia viral vector, a herpes simplex viral vector, an adenovirus associated vector, a lentiviral vector, or any combination thereof.

A "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" may include a tumor. Examples of cancers that may be treated by the methods disclosed herein include, but are not limited to, cancers of the immune system including lymphoma, leukemia, myeloma, and other leukocyte malignancies. In some embodiments, the methods disclosed herein may be used to reduce the tumor size of a tumor derived from, for example, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T cell lymphoma, environmentally induced cancers including those induced by asbestos, other B cell malignancies, and combinations of said cancers. In some embodiments, the cancer is multiple myeloma. The particular cancer may be responsive to chemo- or radiation therapy or the cancer may be refractory. A refractor cancer refers to a cancer that is not amendable to surgical intervention and the cancer is either initially unresponsive to chemo- or radiation therapy or the cancer becomes unresponsive over time.

An "anti-tumor effect" as used herein, refers to a biological effect that may present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect may also refer to the prevention of the occurrence of a tumor, e.g., a vaccine.

A "cytokine," as used herein, refers to a non-antibody protein that is released by one cell in response to contact with a specific antigen, wherein the cytokine interacts with a second cell to mediate a response in the second cell. "Cytokine" as used herein is meant to refer to proteins released by one cell population that act on another cell as intercellular mediators. A cytokine may be endogenously expressed by a cell or administered to a subject. Cytokines may be released by immune cells, including macrophages, B cells, T cells, and mast cells to propagate an immune response. Cytokines may induce various responses in the recipient cell. Cytokines may include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines may promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1α, MIP-1a), MIP-1β (MIP-1b), gamma-induced protein 10 (IP-10), and thymus and activation regulated chemokine (TARC or CCL17).

A "therapeutically effective amount," "effective dose," "effective amount," or "therapeutically effective dosage" of a therapeutic agent, e.g., engineered CAR T cells, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression may be evaluated using a variety of methods known to the skilled practitioner, such as in human subjects during clinical trials, in animal model systems predictive of efficacy in humans, or by assaying the activity of the agent in in vitro assays. An "effective amount" of an agent (e.g., an inhibitor, or combination of inhibitors, of GM-CSF, CSF1, GM-CSFR, or CSF1R) administered to treat one or more symptoms (e.g., encephalopathy, headache, tremor, dizziness, aphasia, delirium, insomnia, and/or anxiety) of an adverse reaction (e.g., neurotoxicity) is any amount that decreases the severity of one or more of those symptoms and/or increases the frequency and duration of symptom-free periods. The terms "effective amount" or "therapeutic effective amount" may, where appropriate, be used interchangeably.

The term "lymphocyte" as used herein includes natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T cells play a major role in cell-mediated-immunity (no antibody involvement). Its T cell receptors (TCR) differentiate themselves from other lymphocyte types. The thymus, a specialized organ of the immune system, is primarily responsible for the T cell's maturation. There are six types of T cells, namely: Helper T cells (e.g., CD4+ cells), Cytotoxic T cells (also known as TC, cytotoxic T lymphocyte, CTL, T-killer cell, cytolytic T cell, CD8+ T cells or killer T cell), Memory T cells ((i) stem memory TSCM cells, like naive cells, are CD45RO−, CCR7+, CD45RA+, CD62L+ (L-selectin), CD27+, CD28+ and IL-7Rα+, but they also express large amounts of CD95, IL-2Rβ, CXCR3, and LFA-1, and show numerous functional attributes distinctive of memory cells); (ii) central memory TCM cells express L-selectin and the CCR7, they secrete IL-2, but not IFNγ or IL-4, and (iii) effector memory TEM cells, however, do not express L-selectin or CCR7 but produce effector cytokines like IFNγ and IL-4), Regulatory T cells (Tregs, suppressor T cells, or CD4+CD25+ regulatory T cells), Natural Killer T cells (NKT) and Gamma Delta T cells. B-cells, on the other hand, play a principal role in humoral immunity (with antibody involvement). It makes antibodies and antigens and performs the role of antigen-presenting cells (APCs) and turns into memory B-cells after activation by antigen interaction. In mammals, immature B-cells are formed in the bone marrow, where its name is derived from.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell, which may either be obtained from a patient or a donor. The cell may be modified to express an exogenous construct, such as, e.g., a chimeric antigen receptor (CAR) or a T cell receptor (TCR), which is incorporated into the cell's genome.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy may include adoptive T cell therapy, tumor-infiltrating lymphocyte (TIL) immunotherapy, autologous cell therapy, engineered autologous cell therapy (eACT™), and allogeneic T cell transplantation. However, one of skill in the art would recognize that the conditioning methods disclosed herein would enhance the effectiveness of any transplanted T cell therapy. Examples of T cell therapies are described in U.S. Patent Publication Nos. 2014/0154228 and 2002/0006409, U.S. Pat. Nos. 7,741,465, 6,319,494, 5,728,388, and International Publication No. WO 2008/081035.

The T cells of the immunotherapy may come from any source known in the art. For example, T cells may be differentiated in vitro from a hematopoietic stem cell population, or T cells may be obtained from a subject. T cells may be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells may be derived from one or more T cell lines available in the art. T cells may also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety.

The term "engineered Autologous Cell Therapy," which may be abbreviated as "eACT™," also known as adoptive cell transfer, is a process by which a patient's own T cells are collected and subsequently genetically altered to recognize and target one or more antigens expressed on the cell surface of one or more specific tumor cells or malignancies. T cells may be engineered to express, for example, chimeric antigen receptors (CAR). CAR positive (+) T cells are engineered to express an extracellular single chain variable fragment (scFv) with specificity for a particular tumor antigen linked to an intracellular signaling part comprising at least one costimulatory domain and at least one activating domain. The CAR scFv may be designed to target, for example, CD19, which is a transmembrane protein expressed by cells in the B cell lineage, including all normal B cells and B cell malignances, including but not limited to diffuse large B-cell lymphoma (DLBCL) not otherwise specified, primary mediastinal large B-cell lymphoma, high grade B-cell lymphoma, and DLBCL arising from follicular lymphoma, NHL, CLL, and non-T cell ALL. Example CAR T cell therapies and constructs are described in U.S. Patent Publication Nos. 2013/0287748, 2014/0227237, 2014/0099309, and 2014/0050708, and these references are incorporated by reference in their entirety.

A "patient" as used herein includes any human who is afflicted with a cancer (e.g., a lymphoma or a leukemia). The terms "subject" and "patient" are used interchangeably herein.

As used herein, the term "in vitro cell" refers to any cell which is cultured ex vivo. In particular, an in vitro cell may include a T cell.

The terms "peptide," "polypeptide," and "protein" are used interchangeably, and refer to a compound comprised of amino acid residues covalently linked by peptide bonds. A protein or peptide contains at least two amino acids, and no limitation is placed on the maximum number of amino acids that may comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Stimulation," as used herein, refers to a primary response induced by binding of a stimulatory molecule with its cognate ligand, wherein the binding mediates a signal transduction event. A "stimulatory molecule" is a molecule on a T cell, e.g., the T cell receptor (TCR)/CD3 complex, that specifically binds with a cognate stimulatory ligand present on an antigen present cell. A "stimulatory ligand" is a ligand that when present on an antigen presenting cell (e.g., an APC, a dendritic cell, a B-cell, and the like) may specifically bind with a stimulatory molecule on a T cell, thereby mediating a primary response by the T cell, including, but not limited to, activation, initiation of an immune response, proliferation, and the like. Stimulatory ligands include, but are not limited to, an anti-CD3 antibody, an MHC Class I molecule loaded with a peptide, a superagonist anti-CD2 antibody, and a superagonist anti-CD28 antibody.

A "costimulatory signal," as used herein, refers to a signal, which in combination with a primary signal, such as TCR/CD3 ligation, leads to a T cell response, such as, but not limited to, proliferation and/or upregulation or down regulation of key molecules.

A "costimulatory ligand," as used herein, includes a molecule on an antigen presenting cell that specifically binds a cognate co-stimulatory molecule on a T cell. Binding of the costimulatory ligand provides a signal that mediates a T cell response, including, but not limited to, proliferation, activation, differentiation, and the like. A costimulatory ligand induces a signal that is in addition to the primary signal provided by a stimulatory molecule, for instance, by binding of a T cell receptor (TCR)/CD3 complex with a major histocompatibility complex (MHC) molecule loaded with peptide. A co-stimulatory ligand may include, but is not limited to, 3/TR6, 4-1BB ligand, agonist or antibody that binds Toll ligand receptor, B7-1 (CD80), B7-2 (CD86), CD30 ligand, CD40, CD7, CD70, CD83, herpes virus entry mediator (HVEM), human leukocyte antigen G (HLA-G), ILT4, immunoglobulin-like transcript (ILT) 3, inducible costimulatory ligand (ICOS-L), intercellular adhesion molecule (ICAM), ligand that specifically binds with B7-H3, lymphotoxin beta receptor, MHC class I chain-related protein A (MICA), MEW class I chain-related protein B (MICB), OX40 ligand, PD-L2, or programmed death (PD) L1. A co-stimulatory ligand includes, without limitation, an antibody that specifically binds with a co-stimulatory molecule present on a T cell, such as, but not limited to, 4-1BB, B7-H3, CD2, CD27, CD28, CD30, CD40, CD7, ICOS, ligand that specifically binds with CD83, lymphocyte function-associated antigen-1 (LFA-1), natural killer cell receptor C (NKG2C), OX40, PD-1, or tumor necrosis factor superfamily member 14 (TNFSF14 or LIGHT).

A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, 4-1BB/CD137, B7-H3, BAFFR, BLAME (SLAMF8), BTLA, CD 33, CD 45, CD100 (SEMA4D), CD103, CD134, CD137, CD154, CD16, CD160 (BY55), CD18, CD19, CD19a, CD2, CD22, CD247, CD27, CD276 (B7-H3), CD28, CD29, CD3 (alpha; beta; delta; epsilon; gamma; zeta), CD30, CD37, CD4, CD4, CD40, CD49a, CD49D, CD49f, CD5, CD64, CD69, CD7, CD80, CD83 ligand, CD84, CD86, CD8alpha, CD8beta, CD9, CD96 (Tactile), CD1-1a, CD1-1b, CD1-1c, CD1-1d, CDS, CEACAM1, CRT AM, DAP-10, DNAM1 (CD226), Fc gamma receptor, GADS, GITR, HVEM (LIGHTR), IA4, ICAM-1, ICAM-1, ICOS, Ig alpha (CD79a), IL2R beta, IL2R gamma, IL7R alpha, integrin, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, LIGHT, LIGHT (tumor necrosis factor superfamily member 14; TNFSF14), LTBR, Ly9 (CD229), lymphocyte function-associated antigen-1 (LFA-1 (CD11a/CD18), MEW class I molecule, NKG2C, NKG2D, NKp30, NKp44, NKp46, NKp80 (KLRF1), OX40, PAG/Cbp, PD-1, PSGL1, SELPLG (CD162), signaling lymphocytic activation molecule, SLAM (SLAMF1; CD150; IPO-3), SLAMF4 (CD244; 2B4), SLAMF6 (NTB-A; Ly108), SLAMF7, SLP-76, TNF, TNFr, TNFR2, Toll ligand receptor, TRANCE/RANKL, VLA1, or VLA-6, or fragments, truncations, or combinations thereof.

The terms "reducing" and "decreasing" are used interchangeably herein and indicate any change that is less than the original. "Reducing" and "decreasing" are relative terms, requiring a comparison between pre- and post-measurements. "Reducing" and "decreasing" include complete depletions.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In some embodiments, "treatment" or "treating" includes a partial remission. In another embodiment, "treatment" or "treating" includes a complete remission.

Various aspects of the disclosure are described in further detail in the following subsections.

Chimeric Antigen Receptors (CAR)

Chimeric antigen receptors (CARs or CAR-Ts) and the T cell receptors (TCRs) of the disclosure are genetically engineered receptors. These engineered receptors may be readily inserted into and expressed by immune cells, including T cells, in accordance with techniques known in the art. With a CAR, a single receptor may be programmed to both recognize a specific antigen and, when bound to that antigen, activate the immune cell to attack and destroy the cell bearing or expressing that antigen. When these antigens exist on tumor cells, an immune cell that expresses the CAR may target and kill the tumor cell.

An aspect of the present disclosure is a chimeric antigen receptor (CAR), or a T cell receptor, which comprises (i) an antigen binding molecule, (ii) a costimulatory domain, and (iii) an activating domain. The costimulatory domain may comprise an extracellular domain, a transmembrane domain, and an intracellular domain. In some embodiments, the extracellular domain comprises a hinge, or a truncated hinge domain.

In some embodiments, the antigen-binding molecule is a molecule that comprises the antigen binding parts (e.g., CDRs) of the antibody from which the molecule is derived. An antigen binding molecule may include the antigenic complementarity determining regions (CDRs). Examples of antigen-binding molecules include, but are not limited to, Fab, Fab', F(ab')2, and Fv fragments, dAb, linear antibodies, scFv antibodies, and multispecific antibodies formed from antigen binding molecules. Peptibodies (i.e., Fc fusion molecules comprising peptide binding domains) are another example of suitable antigen binding molecules. In one embodiment, the CD19 CAR construct comprises an anti-CD 19 single-chain FV. A "Single-chain Fv" or "scFv" antibody binding fragment comprises the variably heavy ($V_H$) and variable light ($V_L$) domains of an antibody, where these domains are present in a single polypeptide chain. Generally, the Fv polypeptide further comprises a polypeptide linker between the $V_H$ and $V_L$ domains, which enables the scFv to form the desired structure for antigen binding. All antibody-related terms used herein take the customary meaning in the art and are well understood by one of ordinary skill in the art.

In some embodiments, the CAR comprises one or more costimulatory domains. In some embodiments, the costimulatory is a signaling region of CD28, OX-40, 4-1BB/CD137, CD2, CD7, CD27, CD30, CD40, programmed death-1 (PD-1), inducible T cell costimulator (ICOS), lymphocyte function-associated antigen-1 (LFA-1 (CD11a/CD18), CD3 gamma, CD3 delta, CD3 epsilon, CD247, CD276 (B7-H3), LIGHT (tumor necrosis factor superfamily member 14; TNFSF14), NKG2C, Ig alpha (CD79a), DAP-10, Fc gamma receptor, MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof.

In some embodiments, the intracellular domain comprises a signaling region of 4-1BB/CD137, activating NK cell receptors, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CDS, CEACAM1, CRT AM, cytokine receptors, DAP-10, DNAM1 (CD226), Fc gamma receptor, GADS, GITR, HVEM (LIGHTR), IA4, ICAM-1, ICAM-1, Ig alpha (CD79a), IL2R beta, IL2R gamma, IL7R alpha, Immunoglobulin-like proteins, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, a ligand that specifically binds with CD83, LIGHT, LIGHT (tumor necrosis factor superfamily member 14; TNFSF14), LTBR, Ly9 (CD229), lymphocyte function-associated antigen-1 (LFA-1 (CD11a/CD18), MHC class I molecule, NKG2C, NKG2D, NKp30, NKp44, NKp46, NKp80 (KLRF1), OX-40, PAG/Cbp, programmed death-1 (PD-1), PSGL1, SELPLG (CD162), signaling lymphocytic activation molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, a Toll ligand receptor, TRANCE/RANKL, VLA1, or VLA-6, or a combination thereof.

In some embodiments, the CAR comprises a hinge region between the transmembrane domain and the binding molecule. In some embodiments, the hinge region is of IgG1, IgG2, IgG3, IgG4, IgA, IgD, IgE, IgM, CD28, or CD8 alpha. In some embodiments, the transmembrane domain is a transmembrane domain of CD28, 4-1BB/CD137, an alpha chain of a T cell receptor, a beta chain of a T cell receptor, CD3 epsilon, CD4, CD5, CD8 alpha, CD9, CD16, CD19, CD22, CD33, CD37, CD45, CD64, CD80, CD86, CD134, CD137, CD154, or a zeta chain of a T cell receptor, or any combination thereof. In some embodiments, the activation domain may be derived from, e.g., any form of CD3-zeta. In some embodiments, the activation domain comes from DAP10, DAP12, or other TCR-type activating signaling molecule.

In one aspect, the present application is directed to CD19 CAR T cell therapy. In one embodiment, the CD19 CAR construct comprises an anti-CD19 scFv domain, an intracellular domain, a transmembrane domain, one or more costimulatory domains, and an activation domain. In one embodiment, the transmembrane domain is derived from transmembrane domain of CD28, 4-1BB/CD137, CD8 alpha, or any combination thereof. In one embodiment, the costimulatory domain is derived from CD8, CD28 OX40, 4-1BB/CD137, or a combination thereof. In one embodiment, the activation domain is derived from CD3zeta. In one embodiment, the CD19 CAR construct comprises a 4-1BB costimulatory domain. In one embodiment, the CD19 CAR construct comprises a CD28 costimulatory domain. In one embodiment, the CD19 CAR construct comprises an anti-CD19 scFv, hinge/transmembrane and costimulatory domains from CD28, and an activation domain from CD3zeta. In one embodiment, the CAR is that expressed in axicabtagene ciloleucel. In one embodiment, the CAR is that is expressed in Kymriah™. Additional CD19 directed CARs that may be used with the methods of the disclosure include, but are not limited to, JCAR017, JCAR015, JCAR014, Uppsala U. anti-CD19 CAR (NCT02132624), and UCART19 (Celectis), See Sadelain et al. Nature Rev. Cancer Vol. 3 (2003), Ruella et al., Curr Hematol Malig Rep., Springer, N.Y. (2016) and Sadelain et al. Cancer Discovery (April 2013).

Engineered T Cells and Use

The T cells of the immunotherapy may be engineered to express any of the CAR described above or others and are referred to as CAR-T cells. CAR-T cells may be engineered to express other molecules and may be of any one of the following exemplary types or others available in the art: first, second, third, fourth, fifth (etc.) CAR-T cells; Armored CAR-T cells, Motile CAR-T cells, TRUCK T-cells, Switch receptor CAR-T cells; Gene edited CAR T-cells; dual receptor CAR T-cells; suicide CAR T-cells, drug-inducible CAR-T cells, synNotch inducible CAR T-cells; and inhibitory CAR T-cells. In one embodiment, the T cells are autologous T-cells. In one embodiment, the T cells are autologous stem cells (for autologous stem cell therapy or ASCT). In one embodiment, the T cells are non-autologous T-cells.

The T cells of the disclosure may come from any source known in the art. For example, T cells may be differentiated in vitro from a hematopoietic stem cell population, or T cells may be obtained from a subject. T cells may be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells may be derived from one or more T cell lines available in the art. T cells may also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, in International Application No. PCT/US2015/014520 (published as WO2015/120096) and in International Application No. PCT/US2016/057983 (published as WO2017/070395), all of which are herein incorporated by reference in their totality for the purposes of describing these methods and in their entirety.

The CD19 CAR-T cells may be prepared by any manufacturing method of preparing T cells for immunotherapy, including, without limitation, those described in International Application No. PCT/US2015/014520 (published as WO2015/120096) and in International Application No. PCT/US2016/057983 (published as WO2017/070395), both of which are herein incorporated by reference in their totality for the purposes of describing these methods; any and all methods used in the preparation of Axicabtagene ciloleucel or Yescarta®; any and all methods used in the preparation of Tisagenlecleucel/Kymriah™; any and all methods used in the preparation of "off-the-shelf" T cells for immunotherapy; and any other methods of preparing lymphocytes for administration to humans. In some embodiments, the manufacturing process is adapted to specifically remove circulating tumor cells from the cells obtained from the patient.

The cells of the present disclosure may be obtained through T cells obtained from a subject. In one embodiment, the T cells may be obtained from, e.g., peripheral blood mononuclear cells, bone marrow, lymph node tissue, cord blood, thymus tissue, tissue from a site of infection, ascites, pleural effusion, spleen tissue, and tumors. In addition, the T cells may be derived from one or more T cell lines available in the art. T cells may also be obtained from a unit of blood collected from a subject using any number of techniques known to the skilled artisan, such as FICOLL™ separation and/or apheresis. In some embodiments, the cells collected by apheresis are washed to remove the plasma fraction and placed in an appropriate buffer or media for subsequent processing. In some embodiments, the cells are washed with PBS. As will be appreciated, a washing step may be used, such as by using a semiautomated flow through centrifuge, e.g., the Cobe™ 2991 cell processor, the Baxter CytoMate™, or the like. In some embodiments, the washed cells are resuspended in one or more biocompatible buffers, or other saline solution with or without buffer. In some embodiments, the undesired components of the apheresis sample are removed. Additional methods of isolating T cells for a T cell therapy are disclosed in U.S. Patent Pub. No. 2013/0287748, which is herein incorporated by references in its entirety.

In some embodiments, T cells are isolated from PBMCs by lysing the red blood cells and depleting the monocytes, e.g., by using centrifugation through a PERCOLL™ gradient. In some embodiments, a specific subpopulation of T cells, such as CD4+, CD8+, CD28+, CD45RA+, and CD45RO+ T cells is further isolated by positive or negative selection techniques known in the art. For example, enrichment of a T cell population by negative selection may be accomplished with a combination of antibodies directed to surface markers unique to the negatively selected cells. In some embodiments, cell sorting and/or selection via negative magnetic immunoadherence or flow cytometry that uses a cocktail of monoclonal antibodies directed to cell surface markers present on the cells negatively selected may be used. For example, to enrich for CD4+ cells by negative selection, a monoclonal antibody cocktail typically includes antibodies to CD8, CD11b, CD14, CD16, CD20, and HLA-DR. In some embodiments, flow cytometry and cell sorting are used to isolate cell populations of interest for use in the present disclosure.

In some embodiments, PBMCs are used directly for genetic modification with the immune cells (such as CARs) using methods as described herein. In some embodiments, after isolating the PBMCs, T lymphocytes are further isolated, and both cytotoxic and helper T lymphocytes are sorted into naive, memory, and effector T cell subpopulations either before or after genetic modification and/or expansion. In some embodiments, CD8+ cells are further sorted into naive, central memory, and effector cells by identifying cell surface antigens that are associated with each of these types of CD8+ cells. In some embodiments, the expression of phenotypic markers of central memory T cells includes CCR7, CD3, CD28, CD45RO, CD62L, and CD127 and are negative for granzyme B. In some embodiments, central memory T cells are CD8+, CD45RO+, and CD62L+ T cells. In some embodiments, effector T cells are negative for CCR7, CD28, CD62L, and CD127 and positive for granzyme B and perforin. In some embodiments, CD4+ T cells are further sorted into subpopulations. For example, CD4+ T helper cells may be sorted into naive, central memory, and effector cells by identifying cell populations that have cell surface antigens.

In some embodiments, the immune cells, e.g., T cells, are genetically modified following isolation using known methods, or the immune cells are activated and expanded (or differentiated in the case of progenitors) in vitro prior to being genetically modified. In another embodiment, the immune cells, e.g., T cells, are genetically modified with the chimeric antigen receptors described herein (e.g., transduced with a viral vector comprising one or more nucleotide sequences encoding a CAR) and then are activated and/or expanded in vitro. Methods for activating and expanding T cells are known in the art and are described, e.g., in U.S. Pat. Nos. 6,905,874; 6,867,041; and 6,797,514; and PCT Publication No. WO 2012/079000, the contents of which are hereby incorporated by reference in their entirety. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). One example is The Dynabeads® system, a CD3/CD28 activator/stimulator system for physiological activation of human T cells. In other embodiments, the T cells are activated and stimulated to proliferate with feeder cells and appropriate antibodies and cytokines using methods such as those described in U.S. Pat. Nos. 6,040,177 and 5,827,642 and PCT Publication No. WO 2012/129514, the contents of which are hereby incorporated by reference in their entirety.

In some embodiments, the T cells are obtained from a donor subject. In some embodiments, the donor subject is human patient afflicted with a cancer or a tumor. In some embodiments, the donor subject is a human patient not afflicted with a cancer or a tumor. In some embodiments, the composition comprises a pharmaceutically acceptable carrier, diluent, solubilizer, emulsifier, preservative and/or adjuvant. In some embodiments, the composition comprises an excipient.

In some embodiments, the composition is selected for parenteral delivery, for inhalation, or for delivery through the digestive tract, such as orally. The preparation of such pharmaceutically acceptable compositions is within the ability of one skilled in the art. In some embodiments, buffers are used to maintain the composition at physiological pH or at a slightly lower pH, typically within a pH range of from about 5 to about 8. In some embodiments, when parenteral administration is contemplated, the composition is in the form of a pyrogen-free, parenterally acceptable aqueous solution comprising a composition described herein, with or without additional therapeutic agents, in a pharmaceutically acceptable vehicle. In some embodiments, the vehicle for parenteral injection is sterile distilled water in which composition described herein, with or without at least one additional therapeutic agent, is formulated as a sterile, isotonic solution, properly preserved. In some embodiments, the preparation involves the formulation of the desired molecule with polymeric compounds (such as polylactic acid or polyglycolic acid), beads or liposomes, that provide for the controlled or sustained release of the product, which are then be delivered via a depot injection. In some embodiments, implantable drug delivery devices are used to introduce the desired molecule.

In some embodiments, the methods of treating a cancer in a subject in need thereof comprise a T cell therapy. In some embodiments, the T cell therapy disclosed herein is engineered Autologous Cell Therapy (eACT™). According to this embodiment, the method may include collecting blood cells from the patient. The isolated blood cells (e.g., T cells) may then be engineered to express a CAR or a TCR disclosed herein. In a particular embodiment, the CAR T cells or the TCR T cells are administered to the patient. In some embodiments, the CAR T cells or the TCR T cells treat a tumor or a cancer in the patient. In some embodiments the CAR T cells or the TCR T cells reduce the size of a tumor or a cancer.

In some embodiments, the donor T cells for use in the T cell therapy are obtained from the patient (e.g., for an autologous T cell therapy). In other embodiments, the donor T cells for use in the T cell therapy are obtained from a subject that is not the patient. The T cells may be administered at a therapeutically effective amount. For example, a therapeutically effective amount of the T cells may be at least about $10^4$ cells, at least about $10^5$ cells, at least about $10^6$ cells, at least about $10^7$ cells, at least about $10^8$ cells, at least about $10^9$, or at least about $10^{10}$. In another embodiment, the therapeutically effective amount of the T cells is about $10^4$ cells, about $10^5$ cells, about $10^6$ cells, about $10^7$ cells, or about $10^8$ cells. In some embodiments, the therapeutically effective amount of the CAR T cells is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg. In some embodiments, the therapeutically effective amount of the CAR-positive viable T cells is between about $1\times10^6$ and about $2\times10^6$ CAR-positive viable T cells per kg body weight up to a maximum dose of about $1\times10^8$ CAR-positive viable T cells. In some embodiments, the therapeutically effective amount of the CAR-positive viable T cells is between about $0.4\times10^8$ and about $2\times10^8$ CAR-positive viable T cells. In some embodiments, the therapeutically effective amount of the CAR-positive viable T cells is about $0.4\times10^8$, about $0.5\times10^8$, about $0.6\times10^8$, about $0.7\times10^8$, about $0.8\times10^8$, about $0.9\times10^8$, about $1.0\times10^8$, about $1.1\times10^8$, about $1.2\times10^8$, about $1.3\times10^8$, about $1.4\times10^8$, about $1.5\times10^8$, about $1.6\times10^8$, about $1.7\times10^8$, about $1.8\times10^8$, about $1.9\times10^8$, or about $2.0\times10^8$ CAR-positive viable T cells.

Methods of Treatment

The methods disclosed herein may be used to treat a cancer in a subject, reduce the size of a tumor, kill tumor cells, prevent tumor cell proliferation, prevent growth of a tumor, eliminate a tumor from a patient, prevent relapse of a tumor, prevent tumor metastasis, induce remission in a patient, or any combination thereof. In some embodiments, the methods induce a complete response. In other embodiments, the methods induce a partial response.

Cancers that may be treated include tumors that are not vascularized, not yet substantially vascularized, or vascularized. The cancer may also include solid or non-solid tumors. In some embodiments, the cancer is a hematologic cancer. In some embodiments, the cancer is of the white blood cells. In other embodiments, the cancer is of the plasma cells. In some embodiments, the cancer is leukemia, lymphoma, or myeloma. In some embodiments, the cancer is acute lymphoblastic leukemia (ALL) (including non T cell ALL), acute lymphoid leukemia (ALL), and hemophagocytic lymphohistocytosis (HLH)), B cell prolymphocytic leukemia, B-cell acute lymphoid leukemia ("BALL"), blastic plasmacytoid dendritic cell neoplasm, Burkitt's lymphoma, chronic lymphocytic leukemia (CLL), chronic myelogenous leukemia (CML), chronic myeloid leukemia (CML), chronic or acute granulomatous disease, chronic or acute leukemia, diffuse large B cell lymphoma, diffuse large B cell lymphoma (DLBCL), follicular lymphoma, follicular lymphoma (FL), hairy cell leukemia, hemophagocytic syndrome (Macrophage Activating Syndrome (MAS), Hodgkin's Disease, large cell granuloma, leukocyte adhesion deficiency, malignant lymphoproliferative conditions, MALT lymphoma, mantle cell lymphoma, Marginal zone lymphoma, monoclonal gammapathy of undetermined significance (MGUS), multiple myeloma, myelodysplasia and myelodysplastic syndrome (MDS), myeloid diseases including but not limited to acute myeloid leukemia (AML), non-Hodgkin's lymphoma (NHL), plasma cell proliferative disorders (e.g., asymptomatic myeloma (smoldering multiple myeloma or indolent myeloma), plasmablastic lymphoma, plasmacytoid dendritic cell neoplasm, plasmacytomas (e.g., plasma cell dyscrasia; solitary myeloma; solitary plasmacytoma; extramedullary plasmacytoma; and multiple plasmacytoma), POEMS syndrome (Crow-Fukase syndrome; Takatsuki disease; PEP syndrome), primary mediastinal large B cell lymphoma (PMBC), small cell- or a large cell-follicular lymphoma, splenic marginal zone lymphoma (SMZL), systemic amyloid light chain amyloidosis, T cell acute lymphoid leukemia ("TALL"), T cell lymphoma, transformed follicular lymphoma, Waldenstrom macroglobulinemia, or a combination thereof.

In some embodiments, the cancer is a myeloma. In some embodiments, the cancer is multiple myeloma. In some embodiments, the cancer is a leukemia. In some embodiments, the cancer is acute myeloid leukemia. in some embodiments, a CD19-directed genetically modified autologous T cell immunotherapy indicated for the treatment of patients with relapsed or refractory large B-cell lymphoma as a first line of therapy, after one line of therapy, or after two or more lines of systemic therapy, including diffuse large B-cell lymphoma (DLBCL) not otherwise specified, primary mediastinal large B-cell lymphoma, high grade B-cell lymphoma, and DLBCL arising from follicular lymphoma. In some embodiments, the cancer is CLL. In some embodiments, the CD19-directed genetically modified autologous T cell immunotherapy is axicabtagene ciloleucel (Axi-cel™, YESCARTA®).

The lines of prior therapy may be any prior anti-cancer therapy, including, but not limited to Bruton Tyrosine Kinase inhibitor (BTKi), check-point inhibitors (e.g., anti-PD1 antibodies, pembrolizumab (Keytruda), Cemiplimab (Libtayo), nivolumab (Opdivo); anti-PD-L1 antibodies, Atezolizumab (Tecentriq), Avelumab (Bavencio), Durvalumab (Imfinzi); anti-CTLA-4 antibodies, Ipilimumab (Yervoy)), anti-CD19 antibodies (e.g. blinatumomab), anti-CD52 antibodies (e.g., alentuzumab); allogeneic stem cell transplantation, anti-CD20 antibodies (e.g., rituximab), systemic chemotherapy, rituximab, anthracycline, ofatumumab, and combination thereof. The prior therapies may also be used in combination with the CD19 CAR T therapies of the disclosure. In one embodiment, the eligible patients may have refractory disease to the most recent therapy or relapse within 1 year after autologous hematopoietic stem cell transplantation (HSCT/ASCT).

In some embodiments, the methods further comprise administering a chemotherapeutic. In some embodiments, the chemotherapeutic selected is a lymphodepleting (preconditioning) chemotherapeutic. Beneficial preconditioning treatment regimens, along with correlative beneficial biomarkers are described in U.S. Provisional Patent Applications 62/262,143 and 62/167,750 which are hereby incorporated by reference in their entirety herein. These describe, e.g., methods of conditioning a patient in need of a T cell therapy comprising administering to the patient specified beneficial doses of cyclophosphamide (between 200 mg/m$^2$/day and 2000 mg/m$^2$/day) and specified doses of fludarabine (between 20 mg/m$^2$/day and 900 mg/m$^2$/day). One such dose regimen involves treating a patient comprising administering daily to the patient about 500 mg/m$^2$/day of cyclophosphamide and about 60 mg/m$^2$/day of fludarabine for three days prior to administration of a therapeutically effective amount of engineered T cells to the patient. In one embodiment, the conditioning regimen comprises cyclophosphamide 500 mg/m$^2$+fludarabine 30 mg/m$^2$ for 3 days. In some embodiments, they are administered at days −4, −3, and −2. In some embodiments, they are administered at days −5, −4, and −3. In one embodiment, the conditioning regimen comprises 900 mg/m$^2$ at day −2 and fludarabine 25 mg/m$^2$ at days −4, −3, −2 (day 0 being the day of administration of the cells. In some embodiments, the conditioning regimen comprises cyclophosphamide 500 mg/m$^2$ daily for two days and fludarabine 30 mg/m$^2$ for 4 days. In some embodiments, the antigen binding molecule, transduced (or otherwise engineered) cells (such as CARs), and the chemotherapeutic agent are administered each in an amount effective to treat the disease or condition in the subject, alone or in combination with other agents and treatments described herein.

In some embodiments, compositions comprising CAR-expressing immune effector cells disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL™, Bristol-Myers Squibb) and doxetaxel (TAXOTERE®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RF S2000; difluoromethylomithine (DMFO); retinoic acid derivatives such as Targretin™ (bexarotene), Panretin™, (alitretinoin); ONTAK™ (denileukin diftitox); esperamicins; capecitabine; and pharmaceutically acceptable salts, acids or derivatives of any of the above. In some embodiments, compositions comprising CAR- and/or TCR-expressing immune effector cells disclosed herein may be administered in conjunction with an anti-hormonal agent that acts to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (Cytoxan®), Doxorubicin (hydroxydoxorubicin), Vincristine (Oncovin®), and Prednisone.

In some embodiments, the chemotherapeutic agent is administered at the same time or within one week after the administration of the engineered cell or nucleic acid. In other embodiments, the chemotherapeutic agent is administered from 1 to 4 weeks or from 1 week to 1 month, 1 week to 2 months, 1 week to 3 months, 1 week to 6 months, 1 week to 9 months, or 1 week to 12 months after the administration of the engineered cell or nucleic acid. In some embodiments, the chemotherapeutic agent is administered at least 1 month before administering the cell or nucleic acid. In some embodiments, the methods further comprise administering two or more chemotherapeutic agents.

A variety of additional therapeutic agents may be used in conjunction with the compositions or agents/treatments described herein. For example, potentially useful additional therapeutic agents include PD-1 inhibitors such as nivolumab (OPDIVO®), pembrolizumab (KEYTRUDA®), pembrolizumab, pidilizumab (CureTech), and atezolizumab (Roche). Additional therapeutic agents suitable for use in combination with the compositions or agents/treatments and methods disclosed herein include, but are not limited to, ibrutinib (IMBRUVICA®), ofatumumab (ARZERRA®), rituximab (RITUXAN®), bevacizumab (AVASTIN®), trastuzumab (HERCEPTIN®), trastuzumab emtansine (KADCYLA®), imatinib (GLEEVEC®), cetuximab (ERBITUX®), panitumumab (VECTIBIX®), catumaxomab, ibritumomab, ofatumumab, tositumomab, brentuximab, alemtuzumab, gemtuzumab, erlotinib, gefitinib, vandetanib, afatinib, lapatinib, neratinib, axitinib, masitinib, pazopanib, sunitinib, sorafenib, tocilizumab, toceranib, lestaurtinib, axitinib, cediranib, lenvatinib, nintedanib, pazopanib, regorafenib, semaxanib, sorafenib, sunitinib, tivozanib, toceranib, vandetanib, entrectinib, cabozantinib, imatinib, dasatinib, nilotinib, ponatinib, radotinib, bosutinib, lestaurtinib, ruxolitinib, pacritinib, cobimetinib, selumetinib, trametinib, binimetinib, alectinib, ceritinib, crizotinib, aflibercept, adipotide, denileukin diftitox, mTOR inhibitors such as Everolimus and Temsirolimus, hedgehog inhibitors such as sonidegib and vismodegib, CDK inhibitors such as CDK inhibitor (palbociclib).

In some embodiments, the composition or agents/treatments comprising CAR immune cells are administered with an anti-inflammatory agent. Anti-inflammatory agents or drugs may include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate. Exemplary NSAIDs include ibuprofen, naproxen, naproxen sodium, Cox-2 inhibitors, and sialylates. Exemplary analgesics include acetaminophen, oxycodone, tramadol of propoxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular), and minocycline.

In some embodiments, the compositions or agents/treatments described herein are administered in conjunction with a cytokine. Examples of cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and -II; erythropoietin (EPO, Epogen®, Procrit®); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1 alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines. In some embodiments, the compositions described herein are administered in conjunction with a steroid.

Administration of CD19-Directed Genetically Modified Autologous T Cell Immunotherapy Indications and Usage In some embodiments, CD19-directed genetically modified autologous T cell immunotherapy indicated for the treatment of adult patients with relapsed or refractory large B-cell lymphoma after two or more lines of systemic therapy, including diffuse large B-cell lymphoma (DLBCL) not otherwise specified, primary mediastinal large B-cell lymphoma, high grade B-cell lymphoma, and DLBCL arising from follicular lymphoma. In some embodiments, CD19-directed genetically modified autologous T cell immunotherapy is not indicated for the treatment of patients with primary central nervous system lymphoma. In some embodiments, the immunotherapy is indicated for the treatment of ALL or CLL. In some embodiments, the immunotherapy is indicated as a first line of therapy. In some embodiments, the immunotherapy is indicated for administration after one line of therapy. Other indications may be found throughout this disclosure.

Dosage and Administration

In some embodiments, an infusion bag of CD19-directed genetically modified autologous T cell immunotherapy comprises a suspension of chimeric antigen receptor (CAR)-positive T cells in approximately 68 mL. The target dose may be between about $1\times10^6$ and about $2\times10^6$ CAR-positive viable T cells per kg body weight, with a maximum of $2\times10^8$ CAR-positive viable T cells. In some embodiments the CD19-directed genetically modified autologous T cell immunotherapy is Axi-cel™ (YESCARTA®, axicabtagene ciloleucel). Amounts of CAR T cells, dosage regimens, methods of administration, subjects, cancers, that fall within the scope of these methods are described elsewhere in this disclosure, alone or in combination with another chemotherapeutic agent, with or without preconditioning, and to any of the patients described elsewhere in the disclosure.

In some embodiments, CD19-directed genetically modified autologous T cell immunotherapy is for autologous use. The patient's identity must match the patient identifiers on the CD19-directed genetically modified autologous T cell immunotherapy cassette and infusion bag. If the information on the patient-specific label does not match the intended patient, the CD19-directed genetically modified autologous T cell immunotherapy cannot be administered. In some embodiments, the availability of CD19-directed genetically modified autologous T cell immunotherapy must be confirmed prior to starting the lymphodepleting regimen. In some embodiments, the immunotherapy is done with allogeneic "off-the-shelf" lymphocytes.

In some embodiments, the patient is pre-treated prior to CD19-directed genetically modified autologous T cell immunotherapy infusion with administration of lymphodepleting chemotherapy. In some embodiments, a lymphodepleting chemotherapy regimen of cyclophosphamide 500 $mg/m^2$ IV and fludarabine 30 $mg/m^2$ IV on the fifth, fourth, and third day before infusion of CD19-directed genetically modified autologous T cell immunotherapy is administered. Other beneficial preconditioning treatment regimens, along with correlative beneficial biomarkers, include those described in U.S. Provisional Patent Applications 62/262,143 and 62/167,750 which are hereby incorporated by reference in their entirety herein. These describe, e.g., methods of conditioning a patient in need of a T cell therapy comprising administering to the patient specified beneficial doses of cyclophosphamide (between 200 $mg/m^2$/day and 2000 $mg/m^2$/day) and specified doses of fludarabine (between 20 $mg/m^2$/day and 900 $mg/m^2$/day). One such dose regimen involves treating a patient comprising administering daily to the patient about 500 $mg/m^2$/day of cyclophosphamide and about 60 $mg/m^2$/day of fludarabine for three days prior to administration of a therapeutically effective amount of engineered T cells to the patient. Other examples of such regimens may be found, for example, in U.S. Pat. No. 9,855,298.

In some embodiments, the patient is premedicated prior to CD19-directed genetically modified autologous T cell immunotherapy infusion by oral administration of acetaminophen at a dose between about 500-1000 mg, about 600-1000 mg, about 700-1000 mg, about 800-1000 mg, about 900-1000 mg, about 500-900 mg, about 500-800 mg, about 500-700 mg, about 500-600 mg, about 600-900 mg, about 600-800 mg, about 600-700 mg, about 700-900 mg, about 700-800 mg, or about 800-900 mg. In some embodiments, the patient is premedicated prior to CD19-directed genetically modified autologous T cell immunotherapy infusion by oral administration of acetaminophen at a dose of about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg or about 1000 mg. In some embodiments, the patient is premedicated prior to CD19-directed genetically modified autologous T cell immunotherapy infusion by administration of acetaminophen 650 mg by mouth and diphenhydramine 12.5 mg intravenously or by mouth approximately 1 hour before CD19-directed genetically modified autologous T cell immunotherapy infusion. In some embodiments, the prophylactic use of systemic steroids is avoided as it may interfere with the activity of CD19-directed genetically modified autologous T cell immunotherapy.

Preparation of CD19-Directed Genetically Modified Autologous T Cell Immunotherapy for Infusion The timing of CD19-directed genetically modified autologous T cell immunotherapy thaw and infusion is coordinated. In some embodiments, the infusion time is confirmed in advance, and the start time of CD19-directed genetically modified autologous T cell immunotherapy thaw is adjusted such that it will be available for infusion when the patient is ready.

In some embodiments, the patient identity is confirmed prior to CD19-directed genetically modified autologous T cell immunotherapy thaw. Prior to CD19-directed genetically modified autologous T cell immunotherapy preparation, patient's identity is matched with the patient identifiers on the CD19-directed genetically modified autologous T cell immunotherapy cassette. In some embodiments, the CD19-directed genetically modified autologous T cell immunotherapy product bag is not removed from the cassette if the information on the patient-specific label does not match the intended patient.

In some embodiments, once patient identification is confirmed, CD19-directed genetically modified autologous T cell immunotherapy product bag is removed from the cassette and the patient information on the cassette label is confirmed to match the bag label. In some embodiments, the method comprises inspecting the product bag for any breaches of container integrity such as breaks or cracks before thawing. In some embodiments, the infusion bag is placed inside a second sterile bag per local guidelines.

In some embodiments, the method comprises thawing the CD19-directed genetically modified autologous T cell immunotherapy at approximately 37° C. using either a water bath or dry thaw method until there is no visible ice in the infusion bag. In some embodiments, the method comprises mixing or agitating the contents of the bag to disperse clumps of cellular material. In some embodiments, the contents of the bag are gently mixed or agitated. In some embodiments, the method comprises inspecting the bag for the presence of visible cell clumps remaining and mixing or agitation is continued. Small clumps of cellular material should disperse with gentle manual mixing. In some embodiments, the method does not comprise a wash, spin down, and/or re-suspension of CD19-directed genetically modified autologous T cell immunotherapy in new media prior to infusion. In some embodiments, once thawed, CD19-directed genetically modified autologous T cell immunotherapy may be stored at room temperature (20° C. to 25° C.) for up to 3 hours. In some embodiments, the immunotherapy is administered immediately.

Administration

In some embodiments, the presently disclosed methods of administration of CD19-directed genetically modified autologous T cell immunotherapy comprise on or more of the following as steps or as considerations:

- Ensure that tocilizumab and emergency equipment are available prior to infusion and during the recovery period.
- Do NOT use a leukodepleting filter.
- Central venous access is recommended for the infusion of CD19-directed genetically modified autologous T cell immunotherapy.
- Confirm the patient's identity matches the patient identifiers on the CD19-directed genetically modified autologous T cell immunotherapy product bag.
- Prime the tubing with normal saline prior to infusion.
- Infuse the entire contents of the CD19-directed genetically modified autologous T cell immunotherapy bag within 30 minutes by either gravity or a peristaltic pump. CD19-directed genetically modified autologous T cell immunotherapy is stable at room temperature for up to 3 hours after thaw.
- Gently agitate the product bag during CD19-directed genetically modified autologous T cell immunotherapy infusion to prevent cell clumping.
- After the entire content of the product bag is infused, rinse the tubing with normal saline at the same infusion rate to ensure all product is delivered.
- CD19-directed genetically modified autologous T cell immunotherapy contains human blood cells that are genetically modified with replication incompetent retroviral vector. Follow universal precautions and local biosafety guidelines for handling and disposal to avoid potential transmission of infectious diseases.

Monitoring

In some embodiments, administration of CD19-directed genetically modified autologous T cell immunotherapy occurs at a certified healthcare facility. In some embodiments, the methods disclosed herein comprise monitoring patients at least daily for 7 days at the certified healthcare facility following infusion for signs and symptoms of CRS and neurologic toxicities. In some embodiments, the methods disclosed herein comprise monitoring patients at least daily for 10 days at the certified healthcare facility following infusion for signs and symptoms of CRS and neurologic toxicities. In some embodiments, patients are instructed to remain within proximity of the certified healthcare facility for at least 4 weeks following infusion.

Management of Severe Adverse Reactions

In some embodiments, the method comprises management of adverse reactions. In some embodiments, the adverse reaction is selected from the group consisting of cytokine release syndrome (CRS), a neurologic toxicity, a hypersensitivity reaction, a serious infection, a cytopenia and hypogammaglobulinemia. In some embodiments, Neutralization or Reduction of the CSF/CSFR1 Axis is used, alone or in combination with other treatments, in the prophylaxis or treatment of adverse reactions. In some embodiments, prophylaxis and/or treatment with adverse reactions and their syndromes is done with an agent like tocilizumab (or another anti-IL6/IL6R agent/antagonist) and/or steroids (e.g., corticosteroids).

In some embodiments, the agent is an antagonist or inhibitor of TL-6 or the IL-6 receptor (TL-6R). In some embodiments, the agent is an antibody that neutralizes TL-6 activity, such as an antibody or antigen-binding fragment that binds to TL-6 or IL-6R. For example, in some embodiments, the agent is or comprises tocilizumab (atlizumab) or sarilumab, anti-IL-6R antibodies. In some embodiments, the agent is an anti-IL-6R antibody described in U.S. Pat. No. 8,562,991. In some cases, the agent that targets IL-6 is an anti-TL-6 antibody, such as siltuximab, elsilimomab, ALD518/BMS-945429, sirukumab (CNTO 136), CPSI-2634, ARGX 109, FE301, FM101, or olokizumab (CDP6038). In some embodiments, the agent may neutralize IL-6 activity by inhibiting the ligand-receptor interactions. In some embodiments, the IL-6/IL-6R antagonist or inhibitor is an IL-6 mutein, such as one described in U.S. Pat. No. 5,591,827. In some embodiments, the agent that is an antagonist or inhibitor of IL-6/IL-6R is a small molecule, a protein or peptide, or a nucleic acid.

In some embodiments, other agents that can be used to manage adverse reactions and their symptoms include an antagonist or inhibitor of a cytokine receptor or cytokine. In some embodiments, the cytokine or receptor is IL-10, TL-6, TL-6 receptor, IFNy, IFNGR, IL-2, IL-2R/CD25, MCP-1, CCR2, CCR4, MIP13, CCR5, TNFalpha, TNFR1, such as TL-6 receptor (IL-6R), IL-2 receptor (IL-2R/CD25), MCP-1 (CCL2) receptor (CCR2 or CCR4), a TGF-beta receptor (TGF-beta I, II, or III), IFN-gamma receptor (IFNGR), MIP1P receptor (e.g., CCR5), TNF alpha receptor (e.g., TNFR1), IL-1 receptor (IL1-Ra/IL-1RP), or IL-10 receptor (IL-10R), IL-1, and IL-1Ralpha/IL-1beta. In some embodiments, the agent comprises siltuximab, sarilumab, olokizumab (CDP6038), elsilimomab, ALD518/BMS-945429, sirukumab (CNTO 136), CPSI-2634, ARGX 109, FE301, or FM101. In some embodiments, the agent, is an antagonist or inhibitor of a cytokine, such as transforming growth factor beta (TGF-beta), interleukin 6 (TL-6), interleukin 10 (IL-10), IL-2, MIP13 (CCL4), TNF alpha, IL-1, interferon gamma (IFN-gamma), or monocyte chemoattractant protein-I (MCP-1). In some embodiments, the is one that targets (e.g. inhibits or is an antagonist of) a cytokine receptor, such as TL-6 receptor (IL-6R), IL-2 receptor (IL-2R/CD25), MCP-1 (CCL2) receptor (CCR2 or CCR4), a TGF-beta receptor (TGF-beta I, II, or III), IFN-gamma receptor (IFNGR), MIP1P receptor (e.g., CCR5), TNF alpha receptor (e.g., TNFR1), IL-1 receptor (IL1-Ra/IL-1RP), or IL-10 receptor (IL-10R).

In some embodiments, tocilizumab is administered in a dosage amount of from or from about 1 mg/kg to 10 mg/kg, 2 mg/kg to 8 mg/kg, 2 mg/kg to 6 mg/kg, 2 mg/kg to 4 mg/kg or 6 mg/kg to 8 mg/kg, each inclusive, or the tocilizumab is administered in a dosage amount of at least or at least about or about 2 mg/kg, 4 mg/kg, 6 mg/kg or 8 mg/kg. In some embodiments, tocilizumab is administered in a dosage amount from about 1 mg/kg to 12 mg/kg, such as at or about 10 mg/kg. In some embodiments, tocilizumab is administered by intravenous infusion.

In some embodiments, the signs and symptoms of adverse reactions are selected from the group consisting of fever, hypotension, tachycardia, hypoxia, and chills, include cardiac arrhythmias (including atrial fibrillation and ventricular tachycardia), cardiac arrest, cardiac failure, renal insufficiency, capillary leak syndrome, hypotension, hypoxia, organ toxicity, hemophagocytic lymphohistiocytosis/macrophage activation syndrome (HLH/MAS), seizure, encephalopathy, headache, tremor, dizziness, aphasia, delirium, insomnia anxiety, anaphylaxis, febrile neutropenia, thrombocytopenia, neutropenia, and anemia.

Cytokine Release Syndrome

In some embodiments, the method comprises identifying Cytokine Release Syndrome (CRS) based on clinical presentation. In some embodiments, the method comprises evaluating for and treating other causes of fever, hypoxia, and hypotension. If CRS is observed or suspected, it may be managed according to the recommendations in Table 1, which may also be used in combination with the other treatments of this disclosure, including Neutralization or Reduction of the CSF/CSFR1 Axis. Patients who experience ≥Grade 2 CRS (e.g., hypotension, not responsive to fluids, or hypoxia requiring supplemental oxygenation) should be monitored with continuous cardiac telemetry and pulse oximetry. In some embodiments, for patients experiencing severe CRS, consider performing an echocardiogram to assess cardiac function. For severe or life-threatening CRS, intensive care supportive therapy may be considered. In some embodiments, a biosimilar or equivalent of tocilizumab may be used instead of tocilizumab in the methods disclosed herein. In other embodiments, another anti-IL6R may be used instead of tocilizumab.

TABLE 1

| CRS Grading and Management Guidance | | |
|---|---|---|
| CRS Grade (a) | Tocilizumab | Corticosteroids |
| Grade 1<br>Symptoms require symptomatic treatment only (e.g., fever, nausea, fatigue, headache, myalgia, malaise). | N/A | N/A |
| Grade 2<br>Symptoms require and respond to moderate intervention.<br>Oxygen requirement less than 40% $FiO_2$ or hypotension responsive to fluids or low-dose of one vasopressor or Grade 2 organ toxicity (b). | Administer tocilizumab (c) 8 mg/kg IV over 1 hour (not to exceed 800 mg).<br>Repeat tocilizumab every 8 hours as needed if not responsive to IV fluids or increasing supplemental oxygen.<br>Limit to a maximum of 3 doses in a 24-hour period; maximum total of 4 doses if no clinical improvement in the signs and symptoms of CRS. | Manage per Grade 3 if no improvement within 24 hours after starting tocilizumab. |

TABLE 1-continued

| CRS Grading and Management Guidance | | |
|---|---|---|
| CRS Grade (a) | Tocilizumab | Corticosteroids |
| Grade 3 Symptoms require and respond to aggressive intervention. Oxygen requirement greater than or equal to 40% $FiO_2$ or hypotension requiring high-dose or multiple vasopressors or Grade 3 organ toxicity or Grade 4 transaminitis. | Per Grade 2 | Administer methylprednisolone 1 mg/kg IV twice daily or equivalent dexamethasone (e.g., 10 mg IV every 6 hours). Continue corticosteroids use until the event is Grade 1 or less, then taper over 3 days. If not improving, manage as Grade 4. |
| Grade 4 Life-threatening symptoms. Requirements for ventilator support, continuous veno-venous hemodialysis (CVVHD) or Grade 4 organ toxicity (excluding transaminitis). | Per Grade 2 | Administer methylprednisolone 1000 mg IV per day for 3 days; if improves, then manage as above. Consider alternate immunosuppressants if no improvement or if condition worsens. |

(a) Lee DW et al., (2014). *Current concepts in the diagnosis and management of cytokine release syndrome.* Blood. 2014 Jul. 10; 124(2): 188-195.
(b) Refer to Table 2 for management of neurologic toxicity.
(c) Refer to ACEMTRA ® (tocilizumab) Prescribing Information for details, *https://www.gene.com/download/pdf/actemra_prescribing.pdf* (last accessed Oct. 18, 2017). Initial U.S. approval is indicated to be in 2010.

Neurologic Toxicity

In some embodiments, the method comprises monitoring patients for signs and symptoms of neurologic toxicities (Table 2). In some embodiments, the method comprises ruling out other causes of neurologic symptoms. Patients who experience ≥Grade 2 neurologic toxicities should be monitored with continuous cardiac telemetry and pulse oximetry. Provide intensive care supportive therapy for severe or life-threatening neurologic toxicities. Consider non-sedating, anti-seizure medicines (e.g., levetiracetam) for seizure prophylaxis for any ≥Grade 2 neurologic toxicities. The following treatments may be used in combination with the other treatments of this disclosure, including Neutralization or Reduction of the CSF/CSFR1 Axis.

TABLE 2

| Neurologic Toxicity Grading and Management Guidance | | |
|---|---|---|
| Grading Assessment | Concurrent CRS | No concurrent CRS |
| Grade 2 | Administer tocilizumab per Table 1 for management of Grade 2 CRS. If no improvement within 24 hours after starting tocilizumab, administer dexamethasone 10 mg IV every 6 hours if not already taking other steroids. Continue dexamethasone use until the event is Grade 1 or less, then taper over 3 days. | Administer dexamethasone 10 mg IV every 6 hours. Continue dexamethasone use until the event is Grade 1 or less, then taper over 3 days. |
| | Consider non-sedating, anti-seizure medicines (e.g., levetiracetam) for seizure prophylaxis. | |
| Grade 3 | Administer tocilizumab per Table 1 for management of Grade 2 CRS. In addition, administer dexamethasone 10 mg IV with the first dose of tocilizumab and repeat dose every 6 hours. Continue dexamethasone use until the event is Grade 1 or less, then taper over 3 days. | Administer dexamethasone 10 mg IV every 6 hours. Continue dexamethasone use until the event is Grade 1 or less, then taper over 3 days. |
| | Consider non-sedating, anti-seizure medicines (e.g., levetiracetam) for seizure prophylaxis. | |
| Grade 4 | Administer tocilizumab per Table 1 for management of Grade 2 CRS. Administer methylprednisolone 1000 mg IV per day with first dose of tocilizumab and continue methylprednisolone 1000 mg IV per day for 2 more days; if improves, then manage as above. | Administer methylprednisolone 1000 mg IV per day for 3 days; if improves, then manage as above. |
| | Consider non-sedating, anti-seizure medicines (e.g., levetiracetam) for seizure prophylaxis. | |

In one embodiment, the disclosure provides a method of treating relapsed or refractory large B-cell lymphoma after two or more lines of systemic therapy in a human comprising administering to the human in need thereof CD19-directed genetically modified autologous T cell immunotherapy comprising:

(a) administering to the patient a composition comprising CD19-directed chimeric antigen receptor (CAR) positive viable T cells;
(b) monitoring the patient following administration for signs and symptoms of an adverse reaction; and
(c) if cytokine release syndrome (CRS) greater than Grade 2 is observed in (b), administering tocilizumab at a dose of about 8 mg/kg IV over 1 hour, repeating tocilizumab every 8 hours as needed if not responsive to IV fluids or increasing supplemental oxygen;
(d) if CRS symptoms observed in (b) do not improve after 24 hours of (c), administering methylprednisolone about 1 mg/kg IV twice daily or administering equivalent dexamethasone dose and continuing corticosteroids use until the event is Grade 1 or less, then tapering over 3 days;
(e) if CRS Grade 3 is observed in (b), administering tocilizumab at a dose of 8 mg/kg IV over 1 hour, repeating tocilizumab every 8 hours as needed if not responsive to IV fluids or increasing supplemental oxygen and administering methylprednisolone 1 mg/kg IV twice daily or administering equivalent dexamethasone dose and continuing corticosteroids use until the event is Grade 1 or less, then tapering over 3 days; and
(f) if CRS Grade 4 is observed in (b), administering tocilizumab at a dose of about 8 mg/kg IV over 1 hour, repeating tocilizumab every 8 hours as needed if not responsive to IV fluids or increasing supplemental oxygen and administering about 1,000 mg IV methylprednisolone per day for 3 days.

In another embodiment, the disclosure provides a method of treating relapsed or refractory large B-cell lymphoma after two or more lines of systemic therapy in a patient comprising administering to the patient in need thereof CD19-directed genetically modified autologous T cell immunotherapy comprising:

(a) administering to the patient a composition comprising CD19-directed chimeric antigen receptor (CAR) positive viable T cells;
(b) monitoring the patient following administration for signs and symptoms of an adverse reaction; and
(c) if cytokine release syndrome (CRS) and/or neurologic toxicity is observed, managing cytokine release syndrome (CRS) and/or neurologic toxicity according to Table 1 and/or Table 2.

Additional Safety Management Strategies with Corticosteroids

Administration of corticosteroids and/or tocilizumab at Grade 1 may be considered prophylactic. Supportive care may be provided in all protocols at all CRS and NE severity grades.

In one embodiment of a protocol for management of adverse events related to CRS, tocilizumab and/or corticosteroids are administered as follows: Grade 1 CRS: no tocilizumab; no corticosteroids; Grade 2 CRS: tocilizumab (only in case of comorbidities or older age); and/or corticosteroids (only in case of comorbidities or older age); Grade 3 CRS: tocilizumab; and/or corticosteroids; Grade 4 CRS: tocilizumab; and/or corticosteroids. In another embodiment of a protocol for management of adverse events related to CRS, tocilizumab and/or corticosteroids are administered as follows: Grade 1 CRS: tocilizumab (if no improvement after 3 days); and/or corticosteroids (if no improvement after 3 days); Grade 2 CRS: tocilizumab; and/or corticosteroids; Grade 3 CRS: tocilizumab; and/or corticosteroids; Grade 4 CRS: tocilizumab; and/or corticosteroids, high dose.

In one embodiment of a protocol for management of adverse events related to NE, tocilizumab and/or corticosteroids are administered as follows: Grade 1 NE: no tocilizumab; no corticosteroids; Grade 2 NE: no tocilizumab; no corticosteroids; Grade 3 NE: tocilizumab; and/or corticosteroids (only if no improvement to tocilizumab, standard dose); Grade 4 NE: tocilizumab; and/or corticosteroids.

In another embodiment of a protocol for management of adverse events related to NE, tocilizumab and/or corticosteroids are administered as follows: Grade 1 NE: no tocilizumab; and/or corticosteroids; Grade 2 NE: tocilizumab; and/or corticosteroids; Grade 3 NE: tocilizumab; and/or corticosteroids, high dose; Grade 4 NE: tocilizumab; and/or corticosteroids, high dose.

In one embodiment, corticosteroid treatment is initiated at CRS grade ≥2 and tocilizumab is initiated at CRS grade ≥2. In one embodiment, corticosteroid treatment is initiated at CRS grade ≥1 and tocilizumab is initiated at CRS grade ≥1. In one embodiment, corticosteroid treatment is initiated at NE grade ≥3 and tocilizumab is initiated at CRS grade ≥3. In one embodiment, corticosteroid treatment is initiated at CRS grade ≥1 and tocilizumab is initiated at CRS grade ≥2. In some embodiments, prophylactic use of tocilizumab administered on Day 2 may decrease the rates of Grade ≥3 CRS.

Any corticosteroid may be appropriate for this use. In one embodiment, the corticosteroid is dexamethasone. In some embodiments, the corticosteroid is methylprednisolone. In some embodiments, the two are administered in combination. In some embodiments, glucocorticoids include synthetic and non-synthetic glucocorticoids. Exemplary glucocorticoids include, but are not limited to: alclomethasones, algestones, beclomethasones (e.g. beclomethasone dipropionate), betamethasones (e.g. betamethasone 17 valerate, betamethasone sodium acetate, betamethasone sodium phosphate, betamethasone valerate), budesonides, clobetasols (e.g. clobetasol propionate), clobetasones, clocortolones (e.g. clocortolone pivalate), cloprednols, corticosterones, cortisones and hydrocortisones (e.g. hydrocortisone acetate), cortivazols, deflazacorts, desonides, desoximethasones, dexamethasones (e.g. dexamethasone 21-phosphate, dexamethasone acetate, dexamethasone sodium phosphate), diflorasones (e.g. diflorasone diacetate), diflucortolones, difluprednates, enoxolones, fluazacorts, flucloronides, fludrocortisones (e.g., fludrocortisone acetate), flumethasones (e.g. flumethasone pivalate), flunisolides, fluocinolones (e.g. fluocinolone acetonide), fluocinonides, fluocortins, fluocortolones, fluorometholones (e.g. fluorometholone acetate), fluperolones (e.g., fluperolone acetate), fluprednidenes, flupredni solones, flurandrenolides, fluticasones (e.g. fluticasone propionate), formocortals, halcinonides, halobetasols, halometasones, halopredones, hydrocortamates, hydrocortisones (e.g. hydrocortisone 21-butyrate, hydrocortisone aceponate, hydrocortisone acetate, hydrocortisone buteprate, hydrocortisone butyrate, hydrocortisone cypionate, hydrocortisone hemisuccinate, hydrocortisone probutate, hydrocortisone sodium phosphate, hydrocortisone sodium succinate, hydrocortisone valerate), loteprednol etabonate, mazipredones, medrysones, meprednisones, methylprednisolones (methylprednisolone aceponate, methylprednisolone acetate, methylprednisolone hemi succinate, methylprednisolone sodium succinate), mometasones (e.g., mometasone furoate), paramethasones (e.g., paramethasone acetate), prednicarbates, prednisolones (e.g. prednisolone 25-diethylaminoacetate, prednisolone sodium phosphate, prednisolone 21-hemi succinate, prednisolone acetate; prednisolone farnesylate, prednisolone hemi succinate, prednisolone-21 (beta-D-glucuronide), prednisolone metasulphobenzoate, prednisolone steaglate, prednisolone tebutate, prednisolone tetrahydrophthalate), prednisones, prednivals, prednylidenes, rimexolones, tixocortols, triamcinolones (e.g. triamcinolone acetonide, triamcinolone benetonide, triamcinolone hexacetonide, triamcinolone acetonide 21 palmitate, triamcinolone diacetate). These glucocorticoids and the salts thereof are discussed in detail, for example, in Remington's Pharmaceutical Sciences, A. Osol, ed., Mack Pub. Co., Easton, Pa. (16th ed. 1980) and Remington: The Science and Practice of Pharmacy, 22nd Edition, Lippincott Williams & Wilkins, Philadelphia, Pa. (2013) and any other editions, which are hereby incorporated by reference. In some embodiments, the glucocorticoid is selected from among cortisones, dexamethasones, hydrocortisones, methylprednisolones, prednisolones and prednisones. In an embodiment, the glucocorticoid is dexamethasone. In other embodiments, the steroid is a mineralcorticoid. Any other steroid may be used in the methods provided herein.

The one or more corticosteroids may be administered at any dose and frequency of administration, which may be adjusted to the severity/grade of the adverse event (e.g., CRS and NE). Tables 1 and 2 provide examples of dosage regimens for management of CRS and NE, respectively. In another embodiment, corticosteroid administration comprises oral or IV dexamethasone 10 mg, 1-4 times per day. Another embodiment, sometimes referred to as "high-dose" corticosteroids, comprises administration of IV methylprednisone 1 g per day alone, or in combination with dexamethasone. In some embodiments, the one or more cortico steroids are administered at doses of 1-2 mg/kg per day.

The corticosteroid may be administered in any amount that is effective to ameliorate one or more symptoms associated with the adverse events, such as with the CRS or neurotoxicity. The corticosteroid, e.g., glucocorticoid, can be administered, for example, at an amount between at or about 0.1 and 100 mg, per dose, 0.1 to 80 mg, 0.1 to 60 mg, 0.1 to 40 mg, 0.1 to 30 mg, 0.1 to 20 mg, 0.1 to 15 mg, 0.1 to 10 mg, 0.1 to 5 mg, 0.2 to 40 mg, 0.2 to 30 mg, 0.2 to 20 mg, 0.2 to 15 mg, 0.2 to 10 mg, 0.2 to 5 mg, 0.4 to 40 mg, 0.4 to 30 mg, 0.4 to 20 mg, 0.4 to 15 mg, 0.4 to 10 mg, 0.4 to 5 mg, 0.4 to 4 mg, 1 to 20 mg, 1 to 15 mg or 1 to 10 mg, to a 70 kg adult human subject. Typically, the corticosteroid, such as a glucocorticoid is administered at an amount between at or about 0.4 and 20 mg, for example, at or about 0.4 mg, 0.5 mg, 0.6 mg, 0.7 mg, 0.75 mg, 0.8 mg, 0.9 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg or 20 mg per dose, to an average adult human subject.

In some embodiments, the corticosteroid may be administered, for example, at a dosage of at or about 0.001 mg/kg (of the subject), 0.002 mg/kg, 0.003 mg/kg, 0.004 mg/kg, 0.005 mg/kg, 0.006 mg/kg, 0.007 mg/kg, 0.008 mg/kg, 0.009 mg/kg, 0.01 mg/kg, 0.015 mg/kg, 0.02 mg/kg, 0.025 mg/kg, 0.03 mg/kg, 0.035 mg/kg, 0.04 mg/kg, 0.045 mg/kg, 0.05 mg/kg, 0.055 mg/kg, 0.06 mg/kg, 0.065 mg/kg, 0.07 mg/kg, 0.075 mg/kg, 0.08 mg/kg, 0.085 mg/kg, 0.09 mg/kg, 0.095 mg/kg, 0.1 mg/kg, 0.15 mg/kg, 0.2 mg/kg, 0.25 mg/kg, 0.30 mg/kg, 0.35 mg/kg, 0.40 mg/kg, 0.45 mg/kg, 0.50 mg/kg, 0.55 mg/kg, 0.60 mg/kg, 0.65 mg/kg, 0.70 mg/kg, 0.75 mg/kg, 0.80 mg/kg, 0.85 mg/kg, 0.90 mg/kg, 0.95 mg/kg, 1 mg/kg, 1.05 mg/kg, 1.1 mg/kg, 1.15 mg/kg, 1.20 mg/kg, 1.25 mg/kg, 1.3 mg/kg, 1.35 mg/kg or 1.4 mg/kg, to an average adult human subject, typically weighing about 70 kg to 75 kg.

Generally, the dose of corticosteroid administered is dependent upon the specific corticosteroid, as a difference in potency exists between different corticosteroids. It is typically understood that drugs vary in potency, and that doses can therefore vary, in order to obtain equivalent effects. Equivalence in terms of potency for various glucocorticoids and routes of administration is well known. Information relating to equivalent steroid dosing (in a non-chronotherapeutic manner) may be found in the British National Formulary (BNF) 37, March 1999.

In some embodiments, any of these embodiments is practiced with autologous anti-CD19 CAR T cell therapy is done with axicabtagene ciloleucel prepared by the described in International Application No. PCT/US2016/057983, with or without AKT inhibitor. In some embodiments, this therapy is used to treat patients with ALL. In other embodiments, this therapy is used to treat any other cancer, as set forth elsewhere in the specification. In some embodiments, the patients are adult patients with relapsed/refractory Acute Lymphoblastic Leukemia (ALL). In some embodiments, the patients received conditioning therapy. In some embodiments, the conditioning therapy comprises cyclophosphamide 500 mg/m$^2$ and fludarabine 30 mg/m$^2$ both for 3 days, at days −4, −3, −2 of the treatment (D0). In some embodiments, these patients are administered axicabtagene ciloleucel at $0.5\times10^6$, $1\times10^6$, or $2\times10^6$ CAR+ cells/kg.

In some of these and other embodiments, the patient is administered steroids at Grade 2 for NE. In some embodiments the patient is administered steroids at Grade 3 for NE. In some of these embodiments, the patient is administered tocilizumab in the context of CRS, alone or in combination with steroids. In some other embodiments, the patient is administered anti-IL6 antibodies (e.g. Siltuximab) to manage CRS. In some other embodiments, the patient is administered anti-IL6 antibodies (e.g. Siltuximab) to manage Neurotoxicity (e.g., Neurotoxic Events). In some embodiments, the patient is refractory to anti-IL6 treatment. In some embodiments, the patient receives siltuximab as third-line treatment for CRS, after failure of both tocilizumab and corticosteroid therapy.

Management of Adverse Effects, Safety, and Neurotoxicity by Neutralization or Reduction of the CSF/CSFR1 Axis In some embodiments, axicabtagene ciloleucel treatment is combined with an inhibitor or antagonist of a member of the colony-stimulating factor (CSF) protein family or of their receptors (e.g., CSF1R, CSF2R) for the management of adverse effects, safety, and/or neurotoxicity. These treatments may be used in any setting, including, but not limited to, prophylactically. They may also be used in combination with steroids. The inhibitors or antagonists used in the combination treatment may be, without limitation, antibodies, neutralizers expressed in CAR-T cells, small molecules, and other agents. In some embodiments, treatment with other CD19-directed genetically modified autologous T cell immunotherapy (e.g., axicabtagene ciloleucel; other examples of such immunotherapy are described elsewhere in the specification) is combined with an inhibitor or antagonist of a member of the colony-stimulating factor (CSF) protein family or of their receptors (e.g., CSF1R, CSF2R).

In one embodiment, the CSF family member is GM-CSF (Granulocyte-macrophage colony-stimulating factor, also known as CSF2). GM-CSF may be produced by a number of haemopoietic and nonhaemopoietic cell types upon stimulation, and it may activate/'prime' myeloid populations to produce inflammatory mediators, such as TNF and interleukin 1β (IL1β). In some embodiments, the GM-CSF inhibitor is an antibody that binds to and neutralizes circulating GM-CSF. In some embodiments, the antibody is selected from Lenzilumab; namilumab (AMG203); GSK3196165/MOR103/Otilimab (GSK/MorphoSys), KB002 and KB003 (KaloBios), MT203 (Micromet and Nycomed), and MORAb-022/gimsilumab (Morphotek). In some embodiments, the antibody is a biosimilar of the same. In some embodiments, the antagonist is E21R, a modified form of GM-CSF that antagonizes the function of GM-CSF. In some embodiments, the inhibitor/antagonist is a small molecule.

In one embodiment, the CSF family member is M-CSF (also known as macrophage colony-stimulating factor or CSF1). Non-limiting examples of agents that inhibit or antagonize CSF1 include small molecules, antibodies, chimeric antigen receptors, fusion proteins, and other agents. In one embodiment, the CSF1 inhibitor or antagonist is an anti-CSF1 antibody. In one embodiment, the anti-CSF1 antibody is selected from those made by Roche (e.g., RG7155), Pfizer (PD-0360324), Novartis (MCS110/lacnotuzumab), or a biosimilar version of any one of the same.

In some embodiments, the inhibitor or antagonist inactivates the activity of either the GM-CSF-R-alpha (aka CSF2R) or CSF1R receptors. In some embodiments, the inhibitor is selected from Mavrilimumab (formerly CAM-3001), a fully human GM-CSF Receptor a monoclonal antibody currently being developed by MedImmune, Inc.; cabiralizumab (Five Prime Therapeutics); LY3022855 (IMC-CS4)(Eli Lilly), Emactuzumab, also known as RG7155 or R05509554; FPA008, a humanized mAb (Five Prime/BMS); AMG820 (Amgen); ARRY-382 (Array Biopharma); MCS110 (Novartis); PLX3397 (Plexxikon); ELB041/AFS98/TG3003 (ElsaLys Bio, Transgene), SNDX-6352 (Syndax). In some embodiments, the inhibitor or antagonist is expressed in CAR-T cells. In some embodiments, the inhibitor is a small molecule (e.g. heteroaryl amides, quinolinone series, pyrido-pyrimide series); BLZ945 (Novartis), PLX7486, ARRY-382, Pexidrtinib (also known as PLX3397) or 5-((5-chloro-1H-pyrrolo[2,3-b]pyridin-3-yl)methyl)-N-06-(trifluoromethyl)pyridin-3-yl) methyl)pyridin-2-amine; GW 2580 (CAS 870483-87-7), KÏ20227 (CAS 623142-96-1), AC708 by Ambit Siosciences, or any CSF1R inhibitor listed in Cannarile et al. Journal for ImmunoTherapy of Cancer (2017) 5:53 and US20180371093, incorporated herein by reference for the inhibitors they disclose. Additional neutralizing antibodies to GM-CSF or its receptor have been described in the art, including in, for example, "GM-CSF as a target in inflammatory/autoimmune disease: current evidence and future therapeutic potential" Hamilton, J. A. Expert Rev. Clin. Immunol., 2015; and "Targeting GM-CSF in inflammatory diseases" Wicks, I. P., Roberts, A. W. Nat. Rev. Rheumatol., 2016.

The inhibitor, or combination of inhibitors, of GM-CSF, CSF1, GM-CSFR, or CSF1R, may be administered in different dosages. One of ordinary skill in the art is routinely capable of determining their effective amount and timing of administration. In one embodiment, mavrilimumab and/or lenzilumab may be used in combination with treatment with CD19-directed genetically modified autologous T cell immunotherapy, which may be, in one example, axicabtagene ciloleucel. Other examples of such immunotherapies are described elsewhere in the specification.

In one embodiment, mavrilimumab is administered SQ, IV, or OP/IP at D0 of CAR-T cell treatment. In one embodiment, a single dose of either 100 mg or 150 mg is administered SQ or IP. Mavrilimumab may be administered prior to, concomitantly with, or after administration of axicabtagene ciloleucel. In one embodiment, both drugs are administered on Day zero (D0) of treatment with CAR-T cells. In one embodiment, mavrilimumab is administered at a single dose of 30 mg. In one embodiment, mavrilimumab is administered at a single dose of 50 mg. In some embodiments, mavrilimumab is administered at a dose of 10 to 500 mg, 100 to 200 mg, 30 to 100 mg, or 30 to 150 mg. In one embodiment, mavrilimumab is administered once at 1 mg/kg of body weight, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, or 30 mg/kg, subcutaneously, OP/IP, or IV, preferably on Day 0. In one embodiment, mavrilimumab is administered once at 3 mg/kg of body weight, preferably on Day 0 mavrilimumab may be administered as a single dose or in multiple doses (e.g., every week, every other week). In one embodiment, mavrilimumab is administered as a single dose between 0.01-10.0 mg/kg, SQ, IV, or IP.

In one embodiment, lenzilumab is administered at 10 mg/kg (600 mg max), 20 mg/kg (1200 mg max), or 30 mg/kg (1800 mg max) via IP infusion. Lenzilumab may be administered prior to, concomitantly with, or after administration of axicabtagene ciloleucel. In one embodiment, both drugs are administered on D0. In one embodiment, lenzilumab is administered as a single dose between 0.01-50.0 mg/kg. In one embodiment, the single dose is 1, 3, 10, 50, or 100 mg/kg. In one embodiment, the single dose is 200 mg, 400 mg, or 600 mg. In one embodiment, lenzilumab is administered at a weekly dosing of 10, 50, or 100 mg/kg.

In one embodiment, the inhibitor or antagonist of GM-CSF, M-CSF, GM-CSF-R-alpha (aka CSF2R) or CSF1R receptors (e.g., mavrilimumab or lenzilumab) maybe administered any day between Day −5 and Day 5 relative to the start of treatment with CD19-directed genetically modified autologous T cell immunotherapy (D0). In one embodiment, the inhibitor is administered any day between Day −2 and Day 10, in one or more daily doses. In one embodiment, the inhibitor is administered one or more weeks after the immunotherapy is started (D0).

Without being bound to any theory, it is hypothesized that inhibition of GM-CSF receptor (such as mavrilimumab) or BM-CSF (such as lenzilumab) may neutralize the elaboration of some cytokines from the myeloid cells or compartment and thus reduces the extent of neuroinflammation. Under such scenario, the incidence of Grade 1, 2, 3 or higher neurologic or adverse events may be reduced. This may be observed or determined by several parameters, such as the levels of GM-CSF suppression or inhibition, the levels of CAR T cells, and the levels of cytokines in blood.

In some embodiments, axicabtagene ciloleucel treatment is combined with treatment with an anti-CD20 agent. In some embodiments, the agent is rituximab. In some embodiments, the agent is an antibody selected from Arzerra, Gazyva, ibritumomab tiuxetan, obinutuzumab, ofatumumab, ocrelizumab, veltuzumab, Rituxan Hycela, Rituxan, Bexxar, Zevalin, and biosimilars of the same. These antibodies have been described in J. M. L. Casan, J. Wong, M. J. Northcott, and S. Opat (2018) Anti-CD20 monoclonal antibodies: reviewing a revolution, Hum Vaccin Immunother. 2018; 14(12): 2820-2841 and F. H. Du, E. A. Mills, Y. Mao-Draayer (2017) Next-generation anti-CD20 monoclonal antibodies in autoimmune disease treatment. Autoimmun Highlights. 2017; 8:1-12. doi:10.1007/s13317-017-0100-y, both of which are incorporated herein by reference in their entirety, particularly for exemplary dosage regimens and cancers within the scope of this disclosure.

Dosage Forms and Strengths

In some embodiments, CD19-directed genetically modified autologous T cell immunotherapy is available as a cell suspension for infusion. In some embodiments, a single dose of CD19-directed genetically modified autologous T cell immunotherapy comprises a target dose between about $1\times10^6$ and about $2\times10^6$ CAR-positive viable T cells per kg of body weight (or maximum of $2\times10^8$ CAR-positive viable T cells for patients 100 kg and above) in approximately 68 mL suspension in an infusion bag. In some embodiments, the CD19-directed genetically modified autologous T cell immunotherapy is axicabtagene ciloleucel (YESCARTA®). In some embodiments, a single dose of CD19-directed genetically modified autologous T cell immunotherapy is present in a container. Such container may be sterile. In some embodiments, the container is an infusion bag. In some embodiments, the infusion bag volume is about 100 mL, 150 mL, 200 mL, 250 mL, 300 mL, 500 mL, 750 mL, 1,000 mL, 1,500 mL, 2,000 mL or 3,000 mL.

Risk Evaluation and Mitigation Strategy (REMS)

Because of the risk of CRS and neurologic toxicities, in some embodiments, CD19-directed genetically modified autologous T cell immunotherapy is available through a restricted program under a Risk Evaluation and Mitigation Strategy (REMS). Typical components of the REMS are:

- Healthcare facilities that dispense and administer CD19-directed genetically modified autologous T cell immunotherapy must be enrolled and comply with the REMS requirements.
- Certified healthcare facilities must have on-site, immediate access to tocilizumab, and ensure that a minimum of two doses of tocilizumab are available for each patient for infusion within 2 hours after CD19-directed genetically modified autologous T cell immunotherapy infusion, if needed for treatment of CRS.
- Certified healthcare facilities must ensure that healthcare providers who prescribe, dispense or administer CD19-directed genetically modified autologous T cell immunotherapy are trained about the management of CRS and neurologic toxicities.

Cytokine Release Syndrome (CRS)

In some embodiments, the health care facility ensures that two doses of tocilizumab are available prior to infusion of CD19-directed genetically modified autologous T cell immunotherapy. In some embodiments, the health care facility ensures that four doses of tocilizumab are available prior to infusion of CD19-directed genetically modified autologous T cell immunotherapy. In some embodiments, the method comprises monitoring patients at least daily for 7 days at the certified healthcare facility following infusion for signs and symptoms of CRS. In some embodiments, the method comprises monitoring patients at least daily for 7-10 days at the certified healthcare facility following infusion for signs and symptoms of CRS. In some embodiments, the method comprises monitoring patients at least daily for 8 days at the certified healthcare facility following infusion for signs and symptoms of CRS. In some embodiments, the method comprises monitoring patients at least daily for 9 days at the certified healthcare facility following infusion for signs and symptoms of CRS. In some embodiments, the method comprises monitoring patients at least daily for 10 days at the certified healthcare facility following infusion for signs and symptoms of CRS. In some embodiments, the method comprises monitoring patients for signs or symptoms of CRS for 4 weeks after infusion. In some embodiments, the method comprises counseling patients to seek immediate medical attention should signs or symptoms of CRS occur at any time. In some embodiments, the method comprises instituting treatment with supportive care, tocilizumab or tocilizumab and corticosteroids as indicated at the first sign of CRS. Examples of supportive care may be found by one of ordinary skill in the art, including those summarized in the following references, incorporated herein by reference in their entirety: Jennifer N. Brudno and James N. Kochenderfer (2016), Toxicities of chimeric antigen receptor T cells: recognition and management, Blood 2016 127: 3321-3330; Lara L Riegler, Gavin P Jones, and Daniel W Lee (2019) Current approaches in the grading and management of cytokine release syndrome after chimeric antigen receptor T-cell therapy, Ther Clin Risk Manag. 2019; 15: 323-335; and Bradley D Hunter Caron A Jacobson (2019) CAR T-Cell Associated Neurotoxicity: Mechanisms, Clinicopathologic Correlates, and Future Directions, JNCI: Journal of the National Cancer Institute.

Neurologic Toxicities

In some embodiments, the method comprises monitoring patients at least daily for 7 days at the certified healthcare facility following infusion for signs and symptoms of neurologic toxicities. In some embodiments, the method comprises monitoring patients at least daily for 7-10 days at the certified healthcare facility following infusion for signs and symptoms of CRS. In some embodiments, the method comprises monitoring patients at least daily for 10 days at the certified healthcare facility following infusion for signs and symptoms of CRS. In some embodiments, the method comprises monitoring patients for signs or symptoms of neurologic toxicities for 4 weeks after infusion and treat promptly.

Hypersensitivity Reactions

Allergic reactions may occur with the infusion of CD19-directed genetically modified autologous T cell immunotherapy. In some embodiments, serious hypersensitivity reactions including anaphylaxis, may be due to dimethyl sulfoxide (DMSO) or residual gentamicin in CD19-directed genetically modified autologous T cell immunotherapy.

Viral Reactivation

In some embodiments, Hepatitis B virus (HBV) reactivation, in some cases resulting in fulminant hepatitis, hepatic failure and death, may occur in patients treated with drugs directed against B cells. In some embodiments, the method comprises performing screening for HBV, HCV, and HIV in accordance with clinical guidelines before collection of cells for manufacturing.

Prolonged Cytopenias

In some embodiments, patients may exhibit cytopenias for several weeks following lymphodepleting chemotherapy and CD19-directed genetically modified autologous T cell immunotherapy infusion. In some embodiments, the method comprises monitoring blood counts after CD19-directed genetically modified autologous T cell immunotherapy infusion.

Hypogammaglobulinemia

In some embodiments, B-cell aplasia and hypogammaglobulinemia may occur in patients receiving treatment with CD19-directed genetically modified autologous T cell immunotherapy. In some embodiments, the method comprises monitoring immunoglobulin levels after treatment with CD19-directed genetically modified autologous T cell immunotherapy and managing using infection precautions, antibiotic prophylaxis and immunoglobulin replacement.

In some embodiments, vaccination with live virus vaccines is not recommended for at least 6 weeks prior to the start of lymphodepleting chemotherapy, during CD19-directed genetically modified autologous T cell immunotherapy treatment, and until immune recovery following treatment with CD19-directed genetically modified autologous T cell immunotherapy.

Secondary Malignancies

In some embodiments, patients treated with CD19-directed genetically modified autologous T cell immunotherapy may develop secondary malignancies. In some embodiments, the method comprises monitoring life-long for secondary malignancies.

Tumor Lysis Syndrome (TLS)

Patients treated with CD19-directed genetically modified autologous T cell immunotherapy may develop TLS, which may be severe. To minimize risk of TLS, in some embodiments, the method comprises evaluating patients for elevated uric acid or high tumor burden and administering allopurinol, or an alternative prophylaxis, prior to axicabtagene ciloleucel infusion. Signs and symptoms of TLS should be monitored and events managed according to standard guidelines.

Effects on Ability to Drive and Use Machines

Due to the potential for neurologic events, including altered mental status or seizures, patients receiving CD19-directed genetically modified autologous T cell immunotherapy are at risk for altered or decreased consciousness or coordination in the 8 weeks following CD19-directed genetically modified autologous T cell immunotherapy infusion. In some embodiments, the method comprises advising patients to refrain from driving and engaging in hazardous occupations or activities, such as operating heavy or potentially dangerous machinery, during this initial period.

Storage and Handling

In some embodiments, CD19-directed genetically modified autologous T cell immunotherapy is supplied in an infusion bag containing approximately 68 mL of frozen suspension of genetically modified autologous T cells in 5% DMSO and 2.5% albumin (human). In some embodiments, CD19-directed genetically modified autologous T cell immunotherapy is supplied in an infusion bag containing approximately 68 mL of frozen suspension of genetically modified autologous T cells in 5% DMSO and 2.5% albumin (human) (NDC 71287-119-01). In some embodiments, CD19-directed genetically modified autologous T cell immunotherapy comprises Cryostor CS10. In some embodiments, CD19-directed genetically modified autologous T cell immunotherapy comprises 300 mg sodium per infusion. In some embodiments, CD19-directed genetically modified autologous T cell immunotherapy is supplied in an infusion bag containing approximately 50-100 mL, 50-90 mL, 50-80 mL, 50-70 mL, 60-70 mL, 60-75 mL, or 65-75 mL, of suspension of genetically modified autologous T cells in 5% DMSO and 2.5% albumin (human). In some embodiments, CD19-directed genetically modified autologous T cell immunotherapy is supplied in an infusion bag containing less than 100 mL, less than 90 mL, less than 80 mL, less than 70 mL, less than 70 mL, less than 72 mL, or less than 75 mL, of suspension of genetically modified autologous T cells in 5% DMSO and 2.5% albumin (human). In some embodiments, CD19-directed genetically modified autologous T cell immunotherapy is supplied in an infusion bag containing greater than 50 mL, greater than 60 mL, greater than 65 mL, greater than 66 mL, greater than 67 mL, or greater than 68 mL, of suspension of genetically modified autologous T cells in 5% DMSO and 2.5% albumin (human). In some embodiments, the suspension is frozen.

In some embodiments, the CD19-directed genetically modified autologous T cell immunotherapy infusion bag is supplied in ethylene-vinyl acetate cryostorage bag with sealed addition tube and two available spike ports, containing approximately 68 mL of cell dispersion.

In some embodiments, the CD19-directed genetically modified autologous T cell immunotherapy infusion bag is individually packed in a metal cassette. In some embodiments, the CD19-directed genetically modified autologous T cell immunotherapy infusion bag is individually packed in a metal cassette (NDC 71287-119-02). In some embodiments, the CD19-directed genetically modified autologous T cell immunotherapy infusion bag is stored in the vapor phase of liquid nitrogen. In some embodiments, the CD19-directed genetically modified autologous T cell immunotherapy infusion bag is supplied in a liquid nitrogen dry shipper.

In some embodiments, the method comprises matching the identity of the patient with the patient identifiers on the cassette and infusion bag upon receipt. In some embodiments, CD19-directed genetically modified autologous T cell immunotherapy is stored frozen in the vapor phase of liquid nitrogen (less than or equal to minus 150° C.). In some embodiments, the CD19-directed genetically modified autologous T cell immunotherapy is thaw before using.

CAR-T cell treatment may be associated with a variety of adverse events, for example, cerebral edema may be detected in the treatment with CD19 CAR-T as described herein. In one aspect, the application provides a method of recovering from cerebral edema following CD19 CAR-T treatment comprising administering an immunosuppressant that depletes T lymphocytes, such as anti-thymocyte globulin (ATG). In one embodiment, ATG is administered at 2 mg/kg/d, IV. In one embodiment, ATG is administered together with methylprednisolone and/or tocilizumab to reduce systemic cytokine storm. In one embodiment, the ATG is rabbit ATG or equine ATG. In another embodiment, ATG may be administered in one or more doses.

The following non-limiting examples and data illustrate various aspects and features relating to the methods and uses of the cells and therapies of the present disclosure. In some embodiments, the present methods and uses of compounds provide results and data that are surprising, unexpected and contrary thereto. While the utility of the methods of the disclosure is illustrated through the use of several cells or compounds that can be used therewith, it will be understood by those skilled in the art that comparable results are obtainable with various other cells or compounds, as are commensurate with the scope of this disclosure. In the context of these examples, ASCT, means autologous stem cell transplant; DLBCL, diffuse large B cell lymphoma; ECOG, Eastern Cooperative Oncology Group performance status; IPI, International Prognostic Index; PD, progressive disease; PMBCL, primary mediastinal B cell lymphoma; SPD, sum of product diameters; and TFL transformed follicular lymphoma.

EXAMPLES

Example 1

Leukapheresis is a procedure for collecting peripheral blood mononuclear (PBMCs). In this example, subjects or patients with relapsed or refractory aggressive B-cell non-Hodgkin lymphoma undergo leukapheresis to obtain T cells for generating axicabtagene ciloleucel. Eligible patients may have refractory disease to the most recent therapy or relapse within 1 year after autologous hematopoietic stem cell transplantation (HSCT).

After leukapheresis, patients undergo a lymphodepleting regimen, which may comprise cyclophosphamide 500 $mg/m^2$ IV and fludarabine 30 $mg/m^2$ IV, both given on the fifth, fourth, and third day before receiving axicabtagene ciloleucel at a dose of $2\times10^6$ CAR-positive viable T cells/kg (maximum permitted dose: $2\times10^8$ cells) via IV infusion (Day 0). In addition, subjects may receive mavrilimumab or lenzilumab. Mavrilimumab may be administered at a dose of 100 mg or 150 mg. Mavrilimumab may be administered once, on Day 0, SQ, OP/IP, or IV at 3 mg/kg of body weight. Lenzilumab may be administered at a dose of 10 mg/kg (600 mg max), 20 mg/kg (1200 mg max), or 30 mg/kg (1800 mg max). Mavrilimumab and lenzilumab may be administered on day 0 prior to, concomitantly with, or after receiving axicabtagene ciloleucel.

Neurological assessment may be conducted on Day 0, on Day 1, and on every other day during the observation period, which would be 7 days. The common neurologic toxicities may include encephalopathy, headache, tremor, dizziness, aphasia, delirium, insomnia, and anxiety.

The grading scale may be the NCI Common Terminology Criteria for Adverse Events (CTCAE) version 5.0 or other guidelines. To evaluate whether the subjects exhibit reduced or modulated neurologica events, several parameters including the levels of cytokines, GS-CSF, CD19 CAR-T cells, anti-tumor effects, and/or the cytokine/chemokine milieu may be determined at different time, e.g. 28 days, or monthly for at least one, two, three, four, five, six, seven, eight, nine, or ten years.

Without being bound to any theory, it is hypothesized that inhibition of GM-CSF receptor (such as with mavrilimumab) or BM-CSF (such as with lenzilumab) may neutralize the elaboration of some cytokines from the myeloid cells or compartment and thus reduce the extent of neuroinflammation. Under such scenario, the incidence of Grade 1, 2, 3 or higher neurologic or adverse events may be reduced. This may be observed or determined by several parameters, such as the levels of GM-CSF suppression or inhibition, the levels of CAR T cells, and the levels of cytokines in blood.

Additionally, PK and PD analysis may be conducted on blood (levels of antiCD19 CAR T cells) or serum (cytokines) as potential predictive markers for the efficacy and safety of axicabtagene ciloleucel. The cytokines and chemokines may include homeostatic, pro-inflammatory and immune modulating cytokines IL-2, IL-6, IL-10, IL-12p40/p70, IL-15, IL-17a, TNF-α, IFN-γ and GM-CSF; acute phase reactants, such as CRP; chemokines IL-8, MCP-1 and MIP-1α and IP-10; and HLH-related markers such as ferritin and IL-2Rα.

Efficacy is established on the basis of complete remission (CR) rate and duration of response (DOR), as determined by an independent review committee.—Parameters such as objective response rate (ORR), complete remission rate, partial remission rate, and/or duration of response may be used to determine or measure efficacy. The ORR may be determined by 2007 revised International Working Group criteria, as assessed by the independent review committee or other similar guideline. Duration of response parameters may include number of responders, DOR (months) (median, 95% CI, range), DOR if best response is CR and DOR if best response is PR (months; median, 95% CI, range); and median follow up for DOR (months). CR, complete remission; DOR, duration of response; NE, not estimable; PR, partial remission. Among all responders. DOR is measured from the date of first objective response to the date of progression or death from relapse or toxicity. Some of the patient selection parameters include:

1. Relapsed or Refractory large B-cell lymphoma after two or more lines of systemic therapy, including histologically confirmed diffuse large B-cell lymphoma (DLBCL) not otherwise specified, primary mediastinal large B-cell lymphoma, high grade B-cell lymphoma, and DLBCL arising from follicular lymphoma.
2. Subjects must have received adequate prior therapy including at a minimum:
   - anti-CD20 monoclonal antibody unless investigator determines that tumor is CD20 negative, and
   - an anthracycline containing chemotherapy regimen;
3. At least 1 measurable lesion according to the Lugano Response Criteria for Malignant Lymphoma (Cheson et al, 2014).
4. No known history or suspicion of central nervous system involvement by lymphoma
5. ECOG performance status of 0 or 1
6. Adequate bone marrow function as evidenced by:
   - ANC≥1000/uL
   - Platelet ≥75,000/uL
   - Absolute lymphocyte count ≥100/uL
7. Adequate renal, hepatic, cardiac, and pulmonary function as evidenced by:
   - Creatinine clearance (Cockcroft Gault)≥60 mL/min
   - Serum ALT/AST≤2.5 ULN
   - Total bilirubin ≤1.5 mg/dL, except in subjects with Gilbert's Syndrome
   - Cardiac ejection fraction ≥50% with no evidence of clinically significant pericardial effusion as determined by ECHO, and no clinically significant ECG findings
   - No clinically significant pleural effusion
   - Baseline oxygen saturation >92% on room air

Example 2

This study included patients with R/R LBCL (including DLBCL, PMBCL, TFL, and high-grade B cell lymphoma) treated with more than 2 prior therapies. A minimum prior therapy included anti-CD20 antibody or an anthracycline containing chemotherapy. Patients were leukapheresed and received conditioning chemotherapy cyclophosphamide 500 $mg/m^2$ and fludarabine 30 $mg/m^2$, both at days −4, −3, and −2 followed by $2\times10^6$ anti-CD19 CAR T cells/kg at day 0. Patients with high disease burden at screening or baseline received bridging therapy (between leukapheresis and conditioning chemotherapy), which may include rituximab (375 $mg/m^2$ weekly for 3 weeks) in combination with dexamethasone (20 to 40 mg/day or equivalent for 1 to 4 days) or methylprednisolone (1 $g/m^2$ for 1 to 3 days) or bendamustine (90 $mg/m^2$ for 2 days) in combination with rituximab (375 $mg/m^2$ for 1 day), with both bendamustine and rituximab started on the same day. This study applied the revised adverse event management (or revised AE management), where patients showing ≥Grade 1 CRS (cytokine release syndrome) received either tocilizumab or corticosteroid; and patients showing ≥Grade 1 NE (neurologic events) received corticosteroid; and patients showing ≥Grade 2 NE (neurologic events) received either tocilizumab or corticosteroid. Corticosteroids included oral or IV dexamethasone 10 mg, 1-4 times per day, or IV methylprednisone 1 g per day.

Tocilizumab was not administered prophylactically. The primary endpoint was incidence and severity of CRS and NE. It was hypothesized that early use or intervention of corticosteroids or the like at lower severity grades (such as Grade 1 CRS or NE) may facilitate the management of severe CRS and NE, potentially reducing such incidence without affecting response rates. 67% of the patients received bridging therapy (therapy between leukapheresis and conditioning chemotherapy). All patients had evidence of disease after bridging therapy documented by a baseline positron-emission tomography/computed tomography scan (PET-CT). 86% of the patients had DLBCL (diffuse large B cell lymphoma) and 14% TFL (transformed follicular lymphoma). The median age was 63 years (y) (range, 36-73), 67% were male. 81% had disease stage 76% were R/R to ≥second-line therapy and 10% had relapsed post-autologous stem cell transplantation. 67% had 3 or more prior therapies. The tumor burden by sum of product diameter, SPD (range) was 1915 (360-11,487). Grade ≥3 AEs were observed in 95% of patients. The most frequent Grade ≥3 AEs were decreased neutrophil count (33%), anemia (29%), neutropenia (29%) and pyrexia (24%). Grade 1 or 2 NE were observed in 48% of patients; Grade ≥3 NE were observed in 10% of patients. Grade ≥3 NE symptoms were somnolence (10%), confusional state (10%), encephalopathy (5%), and aphasia (5%). No Grade ≥4 NE were observed. Grade 1 CRS was observed in 33% of patients and Grade 2 CRS was observed in 67% of patients. No patients had Grade ≥3 CRS. In the median of 7.7 months follow-up, ORR was 81% with CR of 62% and partial response (PR) of 19%. 5% of the patients had stable disease (SD) and 14% had progressive disease (PD). In a prior study, patients received the same treatment and a different AE management where patients showing ≥Grade 2 CRS and patients showing ≥Grade 2 NE received either tocilizumab or corticosteroid (26% of patients received steroids, and 43% received tocilizumab). Results of the 2-year follow-up showed that the objective response rate (ORR) was 83% with a complete response (CR) rate of 58%, 11% of patients exhibited Grade ≥3 CRS, 32% of patients exhibited NE. Together, the results suggested that early use of corticosteroid did not affect the treatment response and reduced the incidence of severe CRS and/or NEs.

Example 3

In this study, patients with R/R B cell ALL, >5% BM (bone marrow) blasts, and ECOG 0-1 received $2\times10^6$, $1\times10^6$, or $0.5\times10^6$ CD19 CART cells/kg, where autologous anti-CD19 CAR T cells with the same CAR construct as axicabtagene ciloleucel were prepared by the process described in International Application No. PCT/US2016/057983) after conditioning chemotherapy (cyclophosphamide: 900 mg/m$^2$; Fludarabine: 25 mg/m$^2$ Days −4, −3, −2). This process would remove circulating tumor cells.

Revised adverse event management (or revised AE management) was implemented for patients in a $1\times10^6$ dose cohort: corticosteroids were at onset of Grade ≥2 NEs (instead of Grade ≥3) and tocilizumab was used only for active toxicity. The primary endpoint was the dose-limiting toxicity (DLT) rate. Patients with prior allogeneic SCT>100 days and/or prior blinatumomab were included. The median age was 46 y (range, 18-77); 30 patients (66%) had ≥3 prior therapies and the median pre-conditioning BM blasts was 70% (range, 0-97). Six, 23, and 16 patients received 2, 1, and $0.5\times10^6$ cells/kg, respectively. There were no DLTs in the DLT-evaluable pts. The most common Grade ≥3 AEs were hypotension (38%), pyrexia (38%) and thrombocytopenia (31%). Of 41 patients, 68% had CR/CRi and 73% had undetectable MRD. Of 19 patients treated with $1\times10^6$ cells/kg, 16 (84%) had a CR/CRi (CR with incomplete hematologic recovery) and the median event-free survival was 15 months. In 9 patients treated with $1\times10^6$ cells/kg and revised AE management, 2 (22%) had Grade 3 CRS and 1 (11%) had Grade 3 NE. No Grade ≥4 CRS or NEs were observed with the revised AE management. Also, these patients exhibited reduced median duration of NEs, reduced rates of Grade 3/4 NE, Grade ≥3 TEAEs (treatment emergent adverse event), CD19 CAR T cell administration-related TEAEs, and CRS.

In patients treated with $1\times10^6$ CD19 CAR-T cells/kg; 84% who had a CR or CRi were MRD negative. ORR was consistent across main covariates, including refractory subgroup and prior transplant. Revised AE management guidelines that required earlier steroid intervention for neurotoxicity and the use of tocilizumab only in the context of CRS resulted in a lower incidence and severity of CRS and NEs and reduced the duration of NEs.

TABLE 3

Incidence of Treatment-Emergent CRS- and NE-Specific Symptoms

| | $2\times10^6$ (n = 6) | | $1\times10^6$ (n = 23) | | $0.5\times10^6$ (n = 16) | | Overall (n = 45) | |
|---|---|---|---|---|---|---|---|---|
| Event, % | Any | Grade ≥ 3 | Any | Grade ≥ 3 | Any | Grade ≥ 3 | Any | Grade ≥ 3 |
| Any CRS[a,b] | 100 | 50 | 100 | 26 | 81 | 25 | 93 | 29 |
| Pyrexia | 100 | 50 | 87 | 39 | 64 | 1 | 80 | 38 |
| Hypotension | 67 | 50 | 74 | 39 | 50 | 19 | 64 | 33 |
| Sinus | 33 | 0 | 43 | 4 | 13 | 0 | 31 | 2 |
| Tachycardia Chills | 17 | 0 | 39 | 0 | 13 | 0 | 27 | 0 |
| Any NE[b] | 85 | 50 | 87 | 43 | 63 | 25 | 78 | 38 |
| Encephalopathy | 67 | 33 | 48 | 26 | 13 | 13 | 38 | 22 |
| Confusional State | 33 | 17 | 39 | 4 | 31 | 13 | 38 | 22 |
| Tremor | 17 | 0 | 35 | 0 | 25 | 0 | 29 | 0 |

[a]CRS was graded per a modified grading system proposed by Lee DW, et al. *Blood*. 2014;124:188-195.
[b]Individual symptoms of CRS and NEs were graded per National Cancer Institute's Common Terminology Criteria for Adverse Events, v 4.03.
CRS, cytokine release syndrome;
NE, neurologic event.

Example 4

In this study, patients with R/R LBCL (including DLBCL, PMBCL, TFL, and high-grade B cell lymphoma) are enrolled in an open label study evaluating the safety and efficacy of axicabtagene ciloleucel in combination with other therapeutic agents. In Cohort 1: Patients receive rituximab (RITUXAN®) 375 mg/m$^2$ (intravenously) on Day −5, and condition chemotherapy with fludarabine 30 mg/m$^2$ and cyclophosphamide 500 mg/m$^2$ on day −5, −4, and −3. Patients receive axicabtagene ciloleucel at a target dose of $2\times10^6$ anti-CD19 CAR T cells/kg on Day 0. Patients also receive rituximab for 5 additional doses at 28-day intervals after CAR T cell infusion. In Cohort 2: Patients receive lenalidomide 10 mg (REVLIMID®) daily starting 7 days after leukapheresis and continuing through Day 3 after axicabtagene ciloleucel infusion. Condition chemotherapy with fludarabine 30 mg/m$^2$ and cyclophosphamide 500 mg/m$^2$ are administered on day −5, −4, and −3. Patients receive axicabtagene ciloleucel at a target dose of $2\times10^6$ anti-CD19 CAR T cells/kg on Day 0. Patients also receive lenalidomide 20 mg for 5 additional cycles at 28-day intervals (21 on treatment/28 days) after CAR T cell infusion. In both Cohorts, some patients may receive mesna (Mesnex) Dosing per institutional guidelines and administered according to package insert.

The primary outcome measure is Complete Response (CR) Rate CR rate is defined as the incidence of a CR per the Lugano Classification. Secondary Outcome Measures include and not limit to: Percentage of Participants Experiencing Adverse Events; Percentage of Participants Experiencing Clinically Significant Changes in Safety Laboratory Values; Objective Response Rate (ORR, as the incidence of either a CR or a partial response (PR) per the Lugano Classification; Duration of Response (DOR, for participants who experience an objective response and is the time from the first objective response to disease progression per the Lugano Classification; Progression-Free Survival (PFS, as the time from the infusion date to the date of disease progression per Lugano Classification; Overall Survival (OS, as the time from infusion to the date of death; Levels of Axicabtagene Ciloleucel in Blood.

Some of the patient selection parameters include: Histologically proven large B-cell lymphoma (including Diffuse large B-cell lymphoma (DLBCL) not otherwise specified, Primary mediastinal large B-cell lymphoma, DLBCL arising from follicular lymphoma, and High-grade B-cell lymphoma); Chemotherapy-refractory disease (including no response to first-line therapy (primary refractory disease), individuals who are intolerant to first-line therapy chemotherapy are excluded, Progressive Disease (PD) as best response to first-line therapy Stable Disease (SD) as best response after at least 4 cycles of first-line therapy (e.g., 4 cycles of RCHOP) with SD duration no longer than 6 months from last dose of therapy), No response to second or greater lines of therapy (including PD as best response to most recent therapy regimen, SD as best response after at least 2 cycles of last line of therapy with SD duration no longer than 6 months from last dose of therapy); Refractory after Autologous stem cell transplant (ASCT)(including disease progression or relapsed ≤12 months after ASCT (biopsy-proven recurrence in relapsed individuals, if salvage therapy is given after ASCT, the individual has had no response to or relapsed after the last line of therapy); At least 1 measurable lesion according to the Lugano Classification (Lesions that have been previously irradiated will be considered measurable only if progression has been documented following completion of radiation therapy; Individuals must have received adequate prior therapy, including at a minimum anti-CD20 mAb and/or an anthracycline-containing chemotherapy regimen; No evidence, suspicion and/or history of central nervous system (CNS) involvement of lymphoma or detectable cerebrospinal fluid malignant cells or brain metastases; At least 2 weeks or 5 half-lives, whichever is shorter, must have elapsed since any prior systemic therapy at the time the individual is planned for leukapheresis; Toxicities due to prior therapy must be stable and recovered to ≤Grade 1 (except for clinically non-significant toxicities, such as alopecia); Eastern Cooperative Oncology Group (ECOG) performance status of 0 or 1; Absolute neutrophil count (ANC)≥1500/μL. Growth factor 7 days prior to screening is not allowed to meet ANC eligibility criteria; Platelet count ≥100,000/μL. Transfusion 7 days prior to screening is not allowed to meet platelet eligibility criteria; Absolute lymphocyte count ≥100/μL; Adequate renal, hepatic, pulmonary, and cardiac function defined as creatinine clearance (as estimated by Cockcroft Gault)≤60 mL/min, serum alanine aminotransferase (ALT)/aspartate aminotransferase (AST)≤2.5 upper limit of normal (ULN), total bilirubin ≤1.5 mg/dL, except in individuals with Gilbert's syndrome, cardiac ejection fraction ≥50% and no evidence of pericardial Effusion, no clinically significant pleural effusion, baseline oxygen saturation >92% on room air; Individuals must be able to comply with the requirements of REVLIMID REMS®.

Some of the patient exclusion criteria include: Known CD19 negative or CD20 negative tumor; History of Richter's transformation of Chronic Lymphocytic Leukemia (CLL); Prior lenalidomide or other immunomodulatory imide drug (IMiD) treatment; Prior CAR therapy or other genetically modified T-cell therapy; Hypersensitivity to rituximab; History of severe, immediate hypersensitivity reaction attributed to aminoglycosides; Presence or suspicion of fungal, bacterial, viral, or other infection that is uncontrolled or requiring IV antimicrobials for management, simple urinary tract infection (UTI) and uncomplicated bacterial pharyngitis are permitted if responding to active treatment and after consultation with the sponsor's medical monitor; History of human immunodeficiency virus (HIV) infection or acute or chronic hepatitis B or hepatitis C infection. Individuals with history of hepatitis infection must have cleared their infection as determined by standard serological and genetic testing per current Infectious Diseases Society of America (IDSA) guidelines or applicable country guidelines; History of malignancy other than nonmelanoma skin cancer in situ (eg, cervix, bladder, breast) or low-grade (Gleason ≤6) prostate cancer or surveillance without any plans for treatment, unless disease free for a least 3 years; Autologous SCT within 6 weeks of planned enrollment; Prior organ transplantation including prior allogeneic Stem Cell Transplant (SCT); Prior CD19 targeted therapy; In the investigator's judgment, the individual is unlikely to complete all protocol-required study visits or procedures.

Example 5

The anti-CD19 CAR T-cell products used in CD19 CAR-T were manufactured by obtaining leukocytes from the leukapheresis product and enriched by selection for CD4+/CD8+ T cells, activated by culturing with anti-CD3 and anti-CD28 antibodies, and transduced with a retroviral vector containing an anti-CD19 CAR gene.

This study described a treatment of a subject with stage IV relapsed/refractory pleomorphic mantle cell lymphoma (MCL) (ibrutinib-refractory). The subject was previously treated with rituximab plus bendamustine (partial remission) with maintenance rituximab (progression), followed by 2 cycles rituximab plus bendamustine (mixed response) with 3 doses maintenance rituximab, approximately 17 cycles of acalabrutinib (complete response followed by progression), and 1 cycle of ibrutinib (progression) which ended 3 weeks prior to leukapheresis. There was no history of prior neurologic disease. Prior to CD19 CAR-T infusion, the patient had an ECOG performance status score of 0, non-bulky disease, and a Ki-67 proliferation index of 80%-90%. Following leukapheresis, the patient received conditioning chemotherapy followed by CD19 CAR-T infusion. Prior to infusion, Prophylactic levetiracetam was initiated and there was no evidence of fever or infection.

Twenty-four hours post-CD19 CAR-T infusion, Grade 1 CRS was observed and treated with tocilizumab (8 mg/kg intravenously (IV)). Vancomycin and aztreonam (each 1 gm IV twice daily) were administered Grade 2 encephalopathy was observed. By Day 3, the subject had leukocytopenia with a white blood cell count of 3.7 K/μL (normal absolute neutrophil count). On Day 4 siltuximab (11 mg/kg IV) was used to treat Grade 2 CRS. Methylprednisolone 500 mg IV twice daily was initiated. Some clinical improvement was observed, but subject's condition deteriorated, and a second dose of tocilizumab was administered. Grade 4 encephalopathy was observed. Mannitol 20% (0.25 mg/kg) every 6 hours was initiated along with steroids and cerebral edema management guidelines were followed. By Day 5, Grade 3 transaminitis was observed. Cerebrospinal fluid (CSF) was clear with an increased opening pressure to 20 cm $H_2O$, elevated CSF protein (600 mg/dL) and glucose (106 mg/dL), and cytology showing increased white blood cells (24 cells/μL) and atypical and activated lymphocytes (mainly T cells) admixed with histiocytes and neutrophils (78%). Intrathecal hydrocortisone and ara-C were administered due to worsening neurologic symptoms. On Day 6, EEG showed bihemispheric cortical dysfunction and MM showed cerebral edema and sulcal hyperintensity. Neurosurgery placed an external ventricular drain to treat the cerebral edema. Prophylactic acyclovir was initiated to mitigate risk of infection.

ATG (2 mg/kg/d IV) was administered along with increased methylprednisolone (1 g twice daily) and a third dose of tocilizumab to dampen systemic cytokine storm. On Day 7, an Mill showed stable changes, and a second dose of ATG was given. Improvement in transaminitis was noted. A third dose of ATG was given on Day 8 after which the transaminitis resolved. Over the next 11 days, he received tapering doses of methylprednisolone with clinical improvement. The ventricular drain was removed on Day 14 and the encephalopathy was resolved. An Mill on Day 20 showed persistent but significantly improved periventricular white matter T2 hyperintensity and resolution of abnormal signal in the dorsal brainstem/thalami. The patient was discharged to a rehabilitation facility with tapering doses of oral steroids. Two months post-CD19 CAR-T, brain MM findings were completely resolved. The patient remains on study, and after 24-months follow-up, is in complete remission with no persistent neurologic or cognitive deficits.

IL-2, a homeostatic cytokine produced by activated CAR T cells, was measured in serum at 16.7 pg/mL on Day 3 and may be associated with CAR T cell expansion. The median at this same time point in the broader cohort was 4.7 pg/mL (IQR, 2.2-10.0), showing a 3.6-fold increase. Post-ATG (Day 7), IL-2 was suppressed (below limit of detection in the assay used), indicating a potential impact of ATG on anti-CD19 CAR T-cell activity. Additional serum biomarker analysis post-CD19 CAR-T indicated increased CAR T cell and myeloid related activity that were controlled. Relative to the broader population, a decline between Day 3 (post-CD19 CAR-T) and Day 7 (post-ATG) in serum interferon (INF)-γ was observed. Serum IFN-γ, a Th1 cytokine and hallmark of CAR T-cell activity, was 584.4 pg/mL at Day 3 and declined to 7.5 pg/mL (lower limit of detection) at Day 7 following ATG administration. By contrast, median IFN-γ in the broader cohort was 97.8 pg/mL (IQR, 24.4-262.4) at Day 3 and 187.7 pg/mL (IQR, 20-1243.6) at Day 7.

Monocyte chemoattractant protein (MCP-1; CCL2), a marker of myeloid-related activity associated with CD19-directed CAR T-cell toxicity, was 1500 pg/ml (above quantitation limit) at Day 3 (cohort median, 712.3 pg/ml [IQR, 517.6-1142.4]), indicating the possibility of excessive myeloid activity post-infusion as a contributing factor. At Day 7, serum MCP-1 was reduced to 96.9 pg/mL (cohort median, 463.8 [IQR, 271.4-954.1]), further demonstrating the impact of ATG in suppressing myeloid-related inflammation.

An analysis of cytokines in CSF taken on Day 8 demonstrated elevated levels of IFNy-induced protein 10 (CXCL10) and MCP-1 compared with those measured in serum on Day 7, as well as elevated intercellular adhesion molecule 1, IL-1 receptor antagonist, and IL-2 receptor alpha (Table S1). Elevated levels of these cytokines in the CSF are consistent with CAR T cell and myeloid trafficking to the central nervous system (CNS) and may have contributed to the NE.

The subject experienced a full recovery with no neurological deficits and achieved a deep and durable response. An improvement in cerebral edema was observed after the administration of ATG, which correlated with an improved transaminitis. Pharmacokinetic and pharmacodynamic results indicated that ATG may have contributed to the resolution of cerebral edema, along with other measures, including corticosteroids, IL-6 or IL-6 receptor blockade with siltuximab or tocilizumab, and a ventriculostomy. The results may lead to revisions in the adverse event management guidelines for NE and CRSS.

Example 6

In Cohorts 1+2 (C1+2) of a study of axicabtagene ciloleucel in patients with refractory LBCL, Grade ≥3 cytokine release syndrome (CRS) and neurologic events (NEs) occurred in 11% and 32% of patients, respectively. Patients received condition chemotherapy with fludarabine 30 $mg/m^2$ and cyclophosphamide 500 $mg/m^2$ on day −5, −4, and −3 and axicabtagene ciloleucel at a target dose of $2\times10^6$ anti-CD19 CAR T cells/kg on Day 0. In C1+2, the objective response rate (ORR) was 83%, the complete response (CR) rate was 58%. A non-randomized safety expansion cohort was added (Cohort 4 [C4]) to evaluate the effect of earlier steroid use on the rates of CRS and NEs. Initial results suggested that early use of steroids may help reduce the incidence of severe CRS and NEs without affecting response rates or CAR T cell expansion.

Eligible patients were leukapheresed, may have receive optional bridging chemotherapy (not allowed in C1+2), and received conditioning chemotherapy (fludarabine and cyclophosphamide) prior to axicabtagene ciloleucel infusion at a target dose of $2\times10^6$ anti-CD19 CAR T cells/kg. Patients in C4 received early steroid intervention starting at Grade 1 NE and at Grade 1 CRS when no improvement was observed after 3 days of supportive care. The primary endpoints were incidence and severity of CRS and NE. Additional endpoints were efficacy outcomes and biomarker analyses, including levels of CAR T cells and inflammatory markers in blood. ORR and CAR T cell levels in C1+2 and 4 were compared across quartiles of tumor burden, the values of which were determined by C1+2.

41 patients received the treatment, with a median follow up of 8.7 months (range, 2.9-13.9 mo). Only one patient had not reached ≥6 mo of follow up due to a delay in dosing after the primary analysis trigger. Patients who received bridging therapy prior to treatment (68%) all had evidence of disease after bridging, documented by a new baseline PET/CT scan. Disease types varied and included DLBCL (63%), TFL (24%), PMBCL (5%), HGBCL (7%). Nearly half of all patients (49%) had an ECOG 1, 70% had disease stage III/IV, 68% were refractory to ≥2nd-line therapy, 12% were relapsed to ≥2nd-line therapy, 63% had ≥3 prior lines of therapy, and 20% had relapsed after ASCT. Overall, patients enrolled in C4 had a lower median tumor burden by sum of product diameters (SPD; C4: 2100 $mm^2$; C1+2: 3723 $mm^2$) and lower pre-Tx serum LDH level compared to C1+2.

A greater proportion of patients in C4 received steroids and tocilizumab vs C1+2 (73% and 76% vs 27% and 43%). Earlier steroid use appeared to impact the percentage of patients with severe CRS or NE: in C4, fewer patients experienced Grade ≥3 CRS (2%) and NE (17%) than was previously observed in C1+2. The ORR in C4 was 73% with a CR rate of 51%. Fifty-four percent of patients remained in ongoing response with ≥6 mo follow up, compared to the 44% ongoing response rate at the primary analysis of C1+2 (also ≥6 mo follow up). While patients in C4 generally had lower SPD than those in C1+2, the responses were comparable between cohorts when evaluated by tumor burden. Median DOR was 8.9 mo, consistent with that observed at the primary analysis of Cohorts 1+2 (8.1 mo; Locke, AACR 2017). Median PFS was 11.7 mo, median OS was not reached. CART cell expansion was comparable between C1+2 and 4: CAR peak levels of 42 cells/μL blood in C1+2 vs 59 cells/μL in C4, and C1+2 had a median CAR AUC of 462 cells/μL×days vs 512 cells/μL in C4. CART cell expansion was also comparable between cohorts when adjusted by tumor burden. Of note, in C4 vs 1+2, there appeared to be lower levels of key biomarkers that are associated with severe NE, including ferritin (pre- and post-Tx), and IL-2 (post-Tx). Earlier steroid use appears to reduce the rate of CAR T cell treatment-related CRS and NEs in C4 compared with C1+2, without a clinically meaningful impact on efficacy, at a median follow up of 8.7 mo.

Example 7

A median follow-up of axicabtagene ciloleucel treatment was 27.1 months in an earlier study, with the overall response rate was 83%, and 39% of the treated patients had ongoing response. Tumor biopsies obtained prior to cell therapy and at relapse were analyzed.

Tumor tissue samples from patients in Cohorts 1 and 2 of the same study described above were analyzed for protein expression of B cell linage markers (CD19, CD20, PAX5, CD79a, and CD22) by multiplex immunohistochemistry (IHC), followed by multiplex immunofluorescence (IF) staining and confocal microscopy in representative cases. Pretreatment tissue samples were available from 96 patients, and 21 were available post-relapse. Paired pretreatment and post-relapse samples were available for 16 patients. CD19 and CD20 H-scores were derived based on proportion and intensity of antigen expression. Scores of 0-5 were considered negative, and scores of 6-300 were considered positive. CD19 splice variants were assessed by RNA sequencing.

Among all patients with available post-relapse samples, 7/21 (33%) showed loss of CD19 expression. Analysis of the 16 paired pretreatment and post-treatment samples showed loss of CD19 expression in 4 patients (25%) who relapsed post-axicabtagene ciloleucel. Nineteen post-relapse tumor samples were evaluable for other B cell lineage markers and showed preservation of CD20, CD22 and CD79a, and the B cell lineage transcription factor PAX5, including in samples with loss or substantial reduction of CD19 expression. Multiplex IF showed that CD19 and CD20 were expressed on the cell membrane, and analysis uncovered the presence of malignant cells with different relative expression levels of these two antigens within a given biopsy. Among the 96 pretreatment tumor samples, IHC analysis showed that CD20 was expressed in nearly all samples, alongside CD19, despite all patients having previously relapsed after receiving rituximab-based regimens. The CD19 and CD20 expression levels in these tumor biopsies obtained pre-cell therapy did not correlate with each other.

RNA sequencing showed alternative splicing of CD19 with loss of exon 2 and/or exons 5/6 in diffuse large B cell lymphoma tumors at baseline and/or relapse, similar to what has been described previously in B cell acute lymphoblastic leukemia. In addition, several novel splice junctions have been identified. The correlation between H-scores and CD19 splice forms and clinical outcomes, including response and progression-free survival were analyzed. In this cohort of patients relapsing after axicabtagene ciloleucel, loss of CD19 expression was common by IHC as compared to pretreatment, which may be related to alternative splicing and selection of variants devoid of target epitope. Additionally, the data showed that expression of alternate B cell lineage antigens was preserved. CD20 cell surface expression was increased in most tumors despite prior rituximab-based treatments.

Example 8

This was a study of post-approval assessment of axicabtagene ciloleucel and to follow the patients for 15 years through the established cellular therapy registry.

The median age overall was 61 years, 101 (34%) patients were ≥65 years, and 197 (67%) patients were male. Baseline clinical characteristics included Eastern Cooperative Oncology Group (ECOG) performance score 0-1 (77%), transformed lymphoma (27%), double-hit lymphoma (36%), prior autologous transplant (34%), and chemotherapy-resistant disease (66%) prior to treatment. The median time from diagnosis to infusion was 18 months (range 2-274 months). Overall response rate (ORR) was 70% (complete response [CR] 52% and partial response [PR] 18%). Patients ≥65 years were generally comparable vs patients <65 with a slightly better CR rate (62% vs 46%, p=0.03) but similar overall response rate (CR+PR, 75% vs 67%, p=0.26). Cytokine release syndrome (CRS) of any grade was reported in 83% of patients. Incidence of Grades ≥3 CRS according to Lee et al 2014 was 11% and was 14% according to American Society for Transplantation and Cellular Therapy (ASTCT) Consensus Grading. Median time to any grade CRS was 3 days (range, 1-17 days), and 94% of CRS cases resolved with a median duration of 7 days (range, 1-121 days). Among patients with CRS, tocilizumab, corticosteroids and siltuximab were used in 70%, 26% and 1% of cases, respectively. Neurologic adverse events (AEs) of any grade occurring after axicabtagene ciloleucel infusion were reported in 181 (61%) patients. One patient was reported to die from cerebral edema. The median time to onset of any grade neurologic AEs was 6 days (range, 1-82 days), and 88% resolved by time of data submission with a median duration of 8 days (range, 1 to 105 days). Corticosteroids were used in 56% of patients for treatment. Patients ≥65 years had comparable CRS (85% vs 82%, p=0.62), grades ≥3 CRS (13% vs 9%, p=0.62), and neurologic AEs (68% vs 58%, p=0.13) vs patients <65 years of age. Prolonged cytopenias (thrombocytopenia and neutropenia), as defined by an inability to recover within 30 days after the administration of axicabtagene ciloleucel, occurred in 7% of patients. Preliminary data reveals 6 patients (2%) reported subsequent neoplasms: myelodysplasia (n=3), lung cancer (n=1), neuroendocrine tumor (n=1), and cutaneous squamous cell carcinoma (n=1).

Example 9

This was a single-arm, Phase 1/2 study in adults with refractory diffuse large B-cell lymphoma (DLBCL), primary mediastinal B-cell lymphoma (PMBCL), or transformed follicular lymphoma (TFL). Refractory disease was defined as no response to last chemotherapy, or relapse ≤12 months post-Autologous Stem Cell Therapy (ASCT). Patients were also required to have an Eastern Cooperative Oncology Group (ECOG) performance status of 0 or 1 and to have received prior treatment with both an anti-CD20 monoclonal antibody and an anthracycline-containing regimen. Following a conditioning regimen of cyclophosphamide (500 mg/m$^2$/day) and fludarabine (30 mg/m$^2$/day) for 3 days, patients received 1 dose of axicabtagene ciloleucel (axi-cel) (2×10$^6$ CAR T cells/kg). Patients were followed for a minimum of 24 months from the axicabtagene ciloleucel infusion (median follow-up was 27.1 months). Safety assessments included all treated patients enrolled in Phases 1 and 2 (≥65 y, n=27; <65 y, n=81). Efficacy assessments included treated patients in Phase 2 only (≥65 y, n=24; <65 y, n=77).

Baseline characteristics were largely similar between patients ≥65 years of age and patients <65 years of age, with some exceptions (Table 4). Most notably, a numerically greater proportion of patients in the ≥65 age group than in the <65 age group had an International Prognostic Index (IPI) score of 3 to 4, which is attributable to age >60 years being a component of IPI scoring. (Shipp M A., H. et al. A predictive model for aggressive non-Hodgkin's lymphoma. The International Non-Hodgkin's Lymphoma Prognostic Factors Project. *N Engl J Med.* 1993; 329(14):987-994). A greater proportion of patients <65 years had received ASCT, as those ≥65 years were less likely to be considered for ASCT. CAR T cell expansion in vivo was similar for patients ≥65 and those <65 years of age (median peak expansion, 43.0 and 35.3 CAR T cells/μL blood, respectively; P=0.769; median area under the curve, 562.0 and 448.4 CAR T cells/μL, respectively, from days 0 to 28; P=0.983).

TABLE 4

Patient Characteristics, efficacy, and safety

| Characteristic | ≥65 y (n = 27) | <65 y (n = 81) |
|---|---|---|
| Median age (range), y | 69 (65-76) | 55 (23-64) |
| Male, n (%) | 22 (81) | 51 (63) |
| ECOG performance status 1, n (%) | 16 (59) | 46 (57) |
| Disease stage III/IV, n (%) | 22 (81) | 68 (84) |
| IPI score 3-4, n (%) | 19 (70) | 29 (36) |
| ≥3 Prior therapies, n (%) | 18 (67) | 58 (72) |
| Median tumor burden by SPD (range), mm$^2$ | 3790 (600-16764) | 3574 (171-23297) |
| Disease type, n (%) | | |
| DLBCL | 20 (74) | 64 (79) |
| PMBCL | 0 | 8 (10) |
| TFL | 7 (26) | 9 (11) |
| Prior ASCT, n (%) | 5 (19) | 24 (30) |
| Refractory subgroup before enrollment, n (%) | | |
| Primary refractory | 1 (4) | 2 (2) |
| Refractory to second- or later-line therapy | 21 (78) | 59 (73) |
| Relapse post-ASCT | 5 (19) | 20 (25) |
| Grade ≥3 AEs* | | |
| Any grade ≥3 AE, n (%) | 27 (100) | 79 (98) |
| Neutropenia† | 20 (74) | 66 (81) |
| Anemia | 13 (48) | 36 (44) |
| Thrombocytopenia‡ | 12 (44) | 31 (38) |
| Decreased white blood cell count | 9 (33) | 22 (27) |
| Encephalopathy | 8 (30) | 17 (21) |
| Lymphocyte count decreased | 8 (30) | 14 (17) |
| Grade ≥3 infection | | |
| Infection, n (%) | 5 (19) | 25 (31) |
| Grade ≥3 CRS§ | | |
| Any grade ≥3 CRS, n (%) | 2 (7) | 10 (12) |
| Pyrexia | 3 (12) | 9 (12) |
| Hypotension | 2 (8) | 8 (11) |
| Hypoxia | 3 (12) | 6 (7) |
| Grade ≥3 NE§ | | |
| Any grade ≥3 NE, n (%) | 12 (44) | 23 (28) |
| Encephalopathy | 8 (30) | 17 (21) |
| Confusional state | 2 (7) | 8 (10) |
| Aphasia | 0 | 8 (10) |
| Agitation | 3 (11) | 2 (2) |
| Delirium | 3 (11) | 0 |

AE, adverse event; CRS, cytokine release syndrome; SPD, sum of product diameter;

*Shown are most common grade ≥3 AEs that occurred in ≥25% of either age group.

†Neutropenia included the terms neutropenia, febrile neutropenia, and neutrophil count decreases.

‡Thrombocytopenia included the terms thrombocytopenia and platelet count decreased.

§Symptoms shown are those that occurred in ≥10% of patients in either age group.

‖Patients in response as of the data cutoff. Efficacy outcomes were analyzed. For this analysis, there were a total of 24 patients ≥65 years old and 77 patients <65 years old. Investigator-assessed objective response rates (ORRs) were comparable (92% vs 81%, respectively). A numerically greater proportion of patients ≥65 than <65 years had complete response (CR) as best response (75% vs 53%, respectively) and ongoing response at data cutoff (42% vs 38%, respectively). The distribution for partial response (PR) was 17% vs 27%, respectively, and the 24-month overall survival rate was 54% vs 49%, respectively.

A similar trend was observed when response rates were assessed by histological subtypes between patients that were ≥65 vs <65 years old. The objective response rate was 92% vs 81%, respectively, for all LBCL; 88% vs 82%, respectively, for DLBCL; and 100% vs 78%, respectively, for TFL patients. The complete response rate was 75% vs 53%, respectively, for all LBCL; 65% vs 50%, respectively, for DLBCL; 100% vs 56%, respectively, for TFL patients; and 75% for PMBCL patients <65 years old.

Median duration of response was 12.0 months vs 8.1 months, ≥65 vs <65 years old, respectively. Median progression-free survival (95% CI) was 13.2 months vs 5.6 months, respectively. Approximately 50% of patients in both age groups were alive at 24 months after treatment (54% vs 49%, respectively). Efficacy outcomes in this trial (ZUMA-1) compared favorably with those reported in the 2017 SCHOLAR-1 study, a pooled, retrospective analysis of 636 DLBCL patients who were resistant to chemotherapy or who relapsed within 12 months of ASCT. (Crump M, et al. Outcomes in refractory diffuse large B-cell lymphoma: results from the international SCHOLAR-1 study. *Blood.* 2017; 130(16):1800-1808). In patients ≥65 and <65 years of age, available therapies in the pre-CAR T cell era resulted in ORRs of only 19% and 27%, respectively, and 2-year survival rates of 19% and 20%, respectively.

Adverse events (AEs) are summarized in Table 4. The most common grade ≥3 AEs were cytopenias, which occurred at similar rates in treated patients ≥65 and <65 years of age. The most common grade ≥3 cytopenia present on or after post-treatment day 93 was neutropenia, which was reported in 15% and 10% of patients ≥65 and <65 years, respectively. Rates of grade ≥3 cytokine release syndrome (CRS) were 7% vs 12%, respectively. Grade ≥3 neurologic events were observed in 44% vs 28%, respectively. Numerically higher rates of some neurologic event-associated symptoms were observed in patients ≥65 years than those <65 years, including grade ≥3 delirium and encephalopathy, which may be consistent with older age. Grade ≥3 infections were reported in 19% vs 31%, respectively. A total of 26% vs 32%, respectively, received intravenous immunoglobulin therapy at the discretion of the investigator. Grade 5 AEs were observed in a total of 4 patients (4% of each age group), as previously reported. Locke F L, et al. Long-term safety and activity of axicabtagene ciloleucel in refractory large B-cell lymphoma (ZUMA-1): a single-arm, multicentre, phase 1-2 trial. *Lancet Oncol.* 2019; 20(1):31-42; Neelapu S S, et al. Axicabtagene ciloleucel CAR T-cell therapy in refractory large B-cell lymphoma. *N Engl J Med.* 2017; 377(26):2531-2544; Locke F L, et al. Phase 1 results of ZUMA-1: a multicenter study of KTE-C19 anti-CD19 CAR T cell therapy in refractory aggressive lymphoma. *Mol Ther.* 2017; 25(1):285-295.

These safety findings are consistent with those of a pooled analysis of 214 patients with large B-cell lymphoma enrolled in clinical trials of tisagenlecleucel and axicabtagene ciloleucel which reported comparable rates of grade ≥3 CRS in patients ≥65 and <65 years of age. Sharma P, et al. A U.S. Food and Drug Administration age based pooled analysis of cytokine release syndrome and neurotoxicity in subjects with relapsed/refractory lymphoma treated with chimeric antigen receptor (CAR) T cell therapy. *Blood.* 2018; 132(Suppl 1):4201-4201. Compared this analysis of ZUMA-1, a subgroup analysis of 300 patients treated with axicabtagene ciloleucel in the standard-of-care setting showed comparable rates of ORR and CRS, but modestly higher rates of complete response and all grade neurological events, in patients ≥65 vs <65 years of age. (Sano D., et al. Safety and efficacy of axicabtagene ciloleucel (axi-cel) in older patients: Results from the US Lymphoma CAR-T Consortium. *Hematological Oncology.* 2019; 37(52):304-305).

In this subgroup analysis of the 2-year follow-up of ZUMA-1, axicabtagene ciloleucel induced a high rate of durable responses with a manageable safety profile, regardless of age. No age-related differences in efficacy, pharmacokinetic profile, or safety were observed, suggesting that age alone may not limit axicabtagene ciloleucel use. Overall, axicabtagene ciloleucel showed substantial clinical benefit for older patients with refractory large B-cell lymphoma, a population for whom treatment options are limited. (Nastoupil L J, et al. Axicabtagene Ciloleucel (Axi-cel) CD19 Chimeric Antigen Receptor (CAR) T-Cell Therapy for Relapsed/Refractory Large B-Cell Lymphoma: Real World Experience. *Blood.* 2018; 132(Suppl 1):abstract 91).

We claim:

1. A method for treating or preventing an adverse reaction in a patient following a treatment with a T cell immunotherapy, comprising administering to the patient a corticosteroid when the patient experiences Grade 1 cytokine release syndrome (CRS).

2. The method of claim 1, further comprising administering to the patient tocilizumab.

3. The method of claim 1, wherein the corticosteroid is dexamethasone.

4. The method of claim 3, wherein the dexamethasone is administered at about 10 mg, about every 6 hours.

5. The method of claim 4, wherein the dexamethasone is administered intravenously.

6. The method of claim 1, wherein the patient has B cell lymphoma (BCL) or acute lymphoblastic leukemia (ALL).

7. The method of claim 6, wherein the patient has relapsed or refractory large B-cell lymphoma after systemic therapy.

8. The method of claim 6, wherein the patient has previously received an anti-CD20 antibody treatment or an anthracycline chemotherapy.

9. The method of claim 1, wherein the T cell immunotherapy comprises T cells engineered to express an anti-CD19 chimeric antigen receptor.

10. The method of claim 9, wherein the T cell immunotherapy comprises axicabtagene ciloleucel.

* * * * *